US011497834B1

(12) United States Patent
Buell et al.

(10) Patent No.: US 11,497,834 B1
(45) Date of Patent: Nov. 15, 2022

(54) SUPERCRITICAL METHOD OF MAKING A BIOCOMPATIBLE COMPOSITE IMPLANT

(71) Applicant: Bio Protectant Technologies, Inc., Dover, DE (US)

(72) Inventors: Joseph Frederick Buell, San Diego, CA (US); Pleasant Fite Hooper, San Diego, CA (US); Brandon Joseph Iglesias, San Diego, CA (US); Chad Joseph Roy, San Diego, CA (US)

(73) Assignee: BIO PROTECTANT TECHNOLOGIES, INC., Dover, DE (US)

( * ) Notice: Subject to any disclaimer, the term of this patent is extended or adjusted under 35 U.S.C. 154(b) by 0 days.

(21) Appl. No.: 17/517,536

(22) Filed: Nov. 2, 2021

(51) Int. Cl.
*A61L 27/38* (2006.01)
*A61L 27/54* (2006.01)
*A61L 27/36* (2006.01)

(52) U.S. Cl.
CPC ........... *A61L 27/54* (2013.01); *A61L 27/3687* (2013.01); *A61L 27/3691* (2013.01); *A61L 2300/208* (2013.01); *A61L 2300/404* (2013.01); *A61L 2300/426* (2013.01); *A61L 2300/602* (2013.01); *A61L 2400/18* (2013.01)

(58) Field of Classification Search
CPC ............... A61L 27/54; A61L 2300/208; A61L 27/3834; A61L 2400/12; A61L 2202/21; A61L 2300/404; A61L 2300/64; D01D 1/02
See application file for complete search history.

(56) References Cited

PUBLICATIONS

Zizovic et al, Supercritical Fluids in the Design of Novel Antimicrobial Materials, Molecules, 25, 2491 (Year: 2020).*

* cited by examiner

*Primary Examiner* — Carlos A Azpuru
(74) *Attorney, Agent, or Firm* — Procopio, Cory, Hargreaves & Savitch LLP

(57) ABSTRACT

Disclosed herein is biocompatible composite material impregnated with antiinfective agents to reduce the rate of infection in patients with medical implants. Also disclosed herein is the utilization of super critical fluid (SCF) methodology to impregnate medical implant materials with antiinfective agents (e.g., antimicrobial, antibiofilm agents, etc.).

29 Claims, 13 Drawing Sheets

Parietex mesh incubated in dye 24 hours ambient conditions and washed

SCF Process
IMPREGNATED HUMAN BONE GRAFT

Human Bone Graft treated with SCF
leached for 3 days in 70% Ethanol then 3 X Water washes and dried Human Bone Graft control SCF Process
IMPREGNATED HUMAN BONE GRAFT Human Bone Graft treated with SCF (Left) and Control (right) incubated in dye 24 hours @ ambient conditions BOTH were then leached for 3 days in 70% Ethanol then 3 X Water washes and dried

SUPERCRITICAL METHOD OF MAKING A BIOCOMPATIBLE COMPOSITE IMPLANT

FIELD OF THE INVENTION

The present invention concerns methods of making biocompatible composite materials having a base material impregnated with a bioprotectant.

SUMMARY

Disclosed herein is the utilization of super critical fluid (SCF) methodology to infuse or impregnate medical implant materials with a bioprotectant (e.g., antimicrobial, antibiofilm agents, immunosuppressant, etc.).

Disclosed herein, in some embodiments, is a medical implant composition, comprising: a base material having a surface portion and an interior portion; and a bioprotectant incorporated throughout the base material, wherein at least a part of the interior portion of the base material is impregnated with the bioprotectant.

In some embodiments, the base material is a surgical mesh material. In some embodiments, the base material is a plastic, a polypropylene, polyester, polytetrafluoroethylene (PTFE), decellularized tissue, bone, tooth, a biosynthetic polymer, or any combination thereof.

In some embodiments, the bioprotectant is an immunosuppressant agent or an anti-infective agent. In some embodiments, the anti-infective agent is an anti-microbial agent, an anti-biofilm agent, or a combination thereof.

In some embodiments, the anti-infective agent is a quaternary ammonium salt. In some embodiments, the quaternary ammonium salt comprises C12 or C14 alkyl chain. In some embodiments, the quaternary ammonium salt is not benzalkonium chloride or a polymeric quaternary ammonium salt. In some embodiments, the quaternary ammonium salt is C12-C14-alkyl(ethylbenzyl)dimethylammonium chloride. In some embodiments, the quaternary ammonium salt is C12-alkyl(ethylbenzyl)dimethylammonium chloride. In some embodiments, the quaternary ammonium salt is C14-alkyl(ethylbenzyl)dimethylammonium chloride.

In some embodiments, the immunosuppressant agent is a calcineurin inhibitors. In some embodiments, the immunosuppressant agent is selected from the group consisting of cyclosporine, tacrolimus, and pimecrolimus. In some embodiments, the immunosuppressant agent is tacrolimus.

In some embodiments, the bioprotectant is heterogeneously impregnated throughout the medical implant material. In some embodiments, the bioprotectant is homogeneously impregnated throughout the medical implant material.

In some embodiments, at least 30% of the interior portion of the base material is impregnated with the bioprotectant. In some embodiments, at least 50% of the interior portion of the base material is impregnated with the bioprotectant. In some embodiments, least 60% of the interior portion of the base material is impregnated with the bioprotectant. In some embodiments, at least 70% of the interior portion of the base material is impregnated with the bioprotectant.

In some embodiments, the composition provides sustained release of the bioprotectant from the composition for at least 7 days upon implantation. In some embodiments, the composition provides sustained release of the bioprotectant from the composition for at least 14 days upon implantation. In some embodiments, the composition provides sustained release of the bioprotectant from the composition for at least 4 weeks upon implantation. In some embodiments, the composition provides sustained release of the bioprotectant from the composition for at least 12 weeks upon implantation.

In some embodiments, the composition retains at least 50% of the bioprotectant 3 days after implantation. In some embodiments, the composition retains at least 70% of the bioprotectant 3 days after implantation. In some embodiments, the composition retains at least 90% of the bioprotectant 3 days after implantation. In some embodiments, the composition retains at least 90% of the bioprotectant 7 days after implantation. In some embodiments, the composition retains at least 90% of the bioprotectant 14 days after implantation. In some embodiments, the composition retains at least 90% of the bioprotectant 28 days after implantation.

In some embodiments, the composition is present in, and provides structural strength to, a medical implant. In some embodiments, the medical implant is selected from the group consisting of a surgical mesh, a breast augmentation implant, a cannula, a catheter, an orthopedic implant, or a hernia repair implant. In some embodiments, the medical implant is a surgical mesh. In some embodiments, the surgical mesh is a synthetic mesh, an acellular mesh, or a hybrid mesh comprising an acellular mesh and a synthetic mesh. In some embodiments, the medical implant is a breast augmentation implant.

In some embodiments, the composition is prepared by a process comprising: contacting the based material and the bioprotectant with supercritical fluid carbon dioxide (SCF—$CO_2$) in an enclosure under an elevated pressure to allow the bioprotectant to impregnate at least a part of the interior portion of the base material. In some embodiments, the process further comprises reducing the pressure within the enclosure after at least a part of the interior portion of the base material is impregnated with the bioprotectant.

In some embodiments, the base material and bioprotectant are placed in the enclosure before SCF—$CO_2$ enters the enclosure. The composition of Embodiment 36-37, wherein the bioprotectant is combined with SCF—$CO_2$ to form a mixture before the mixture contacts the base material in the enclosure. In some embodiments, the elevated pressure is from about 500 psi to about 6000 psi.

In some embodiments, the elevated pressure is from about 500 psi to about 2500 psi. In some embodiments, the elevated pressure is from about 1000 psi to about 2500 psi. In some embodiments, the elevated pressure is from about 1000 psi to about 2000 psi. In some embodiments, the elevated pressure is from about 1500 psi to about 2000 psi. In some embodiments, temperature in the enclosure is from about 15° C. to about 60° C. In some embodiments, temperature in the enclosure is from about 30° C. to about 55° C. In some embodiments, temperature in the enclosure is from about 40° C. to about 50° C. In some embodiments, the base material comprises decellularized tissue.

In some embodiments, the elevated pressure is from about 2500 psi to about 6000 psi. In some embodiments, the elevated pressure is from about 3000 psi to about 6000 psi. In some embodiments, the elevated pressure is from about 3000 psi to about 5000 psi. In some embodiments, the elevated pressure is from about 4000 psi to about 5000 psi. In some embodiments, temperature in the enclosure is from about 60° C. to about 160° C. In some embodiments, temperature in the enclosure is from about 80° C. to about 150° C. In some embodiments, temperature in the enclosure is from about 110° C. to about 130° C. In some embodiments, the base material comprises polypropylene.

In some embodiments, the contact of the base material and the bioprotectant with SCF—$CO_2$ occurs for a period of from about 1 minute to about 24 hours. In some embodiments, the contact of the base material and the bioprotectant with SCF—CO$_2$ occurs for a period of from about 5 minutes to about 10 hours. In some embodiments, the contact of the base material and the bioprotectant with SCF—CO$_2$ occurs for a period of from about 5 minutes to about 8 hours.

Disclosed herein, in some embodiments, is method of preparing a medical implant composition, comprising: (i) placing the base material in an enclosure, wherein the base material comprises a surface portion and an interior portion; (ii) allowing supercritical fluid carbon dioxide (SCF—CO$_2$) to flow into the enclosure and contact the base material in the presence of a bioprotectant at an elevated pressure; (iii) reducing pressure in the enclosure after at least a part of the interior portion of the base material is impregnated with the bioprotectant In some embodiments, the base material and bioprotectant are placed in the enclosure before SCF—CO$_2$ enters the enclosure. In some embodiments, the bioprotectant is combined with SCF—CO$_2$ to form a mixture before the mixture contacts the base material in the enclosure. In some embodiments, the elevated pressure is from about 500 psi to about 6000 psi.

In some embodiments, the elevated pressure is from about 500 psi to about 2500 psi. In some embodiments, the elevated pressure is from about 1000 psi to about 2500 psi. In some embodiments, the elevated pressure is from about 1000 psi to about 2000 psi. In some embodiments, the elevated pressure is from about 1500 psi to about 2000 psi. In some embodiments, temperature in the enclosure is from about 15° C. to about 60° C. during the contact. In some embodiments, temperature in the enclosure is from about 30° C. to about 55° C. during the contact. In some embodiments, temperature in the enclosure is from about 40° C. to about 50° C. during the contact. In some embodiments, the base material comprises decellularized tissue.

In some embodiments, the elevated pressure is from about 2500 psi to about 6000 psi. In some embodiments, the elevated pressure is from about 3000 psi to about 6000 psi. In some embodiments, the elevated pressure is from about 3000 psi to about 5000 psi. In some embodiments, the elevated pressure is from about 4000 psi to about 5000 psi. In some embodiments, temperature in the enclosure is from about 60° C. to about 160° C. during the contact. In some embodiments, temperature in the enclosure is from about 80° C. to about 150° C. during the contact. In some embodiments, temperature in the enclosure is from about 110° C. to about 130° C. during the contact. In some embodiments, the base material comprises polypropylene.

In some embodiments, the contact of the base material and the bioprotectant with SCF—CO$_2$ occurs for a period of from about 1 minute to about 24 hours. In some embodiments, the contact of the base material and the bioprotectant with SCF—CO$_2$ occurs for a period of from about 5 minutes to about 10 hours. In some embodiments, the contact of the base material and the bioprotectant with SCF—CO$_2$ occurs for a period of from about 5 minutes to about 8 hours.

In some embodiments, the contact of SCF—CO$_2$ with the base material occurs in the presence of the bioprotectant and a solvent. In some embodiments, the solvent is combined with bioprotectant prior to the contact of SCF—CO$_2$ with the base material. In some embodiments, the solvent is combined with SCF—CO$_2$ prior to the contact of SCF—CO$_2$ with the base material in the presence of the bioprotectant.

In some embodiments, the base material is a surgical mesh material. In some embodiments, the base material is a plastic, a polypropylene, polyester, polytetrafluoroethylene (PTFE), decellularized tissue, bone, tooth, a biosynthetic polymer, or any combination thereof.

In some embodiments, the bioprotectant is an immunosuppressant agent or an anti-infective microbial agent.

In some embodiments, the anti-infective agent is an anti-microbial agent, an anti-biofilm agent, or a combination thereof. In some embodiments, the anti-infective agent is a quaternary ammonium salt. In some embodiments, the quaternary ammonium salt comprises C12 or C14 alkyl chain. In some embodiments, the quaternary ammonium salt is not benzalkonium chloride or a polymeric quaternary ammonium salt. In some embodiments, the quaternary ammonium salt is C12-C14-alkyl(ethylbenzyl)dimethylammonium chloride. In some embodiments, the quaternary ammonium salt is C12-alkyl(ethylbenzyl)dimethylammonium chloride. In some embodiments, the quaternary ammonium salt is C14-alkyl(ethylbenzyl)dimethylammonium chloride.

In some embodiments, the immunosuppressant agent is a calcineurin inhibitors. In some embodiments, the immunosuppressant agent is selected from the group consisting of cyclosporine, tacrolimus, and pimecrolimus. In some embodiments, the immunosuppressant agent is tacrolimus.

In some embodiments, the bioprotectant is heterogeneously impregnated throughout the medical implant material. In some embodiments, the bioprotectant is homogeneously impregnated throughout the medical implant material.

In some embodiments, at least 30% of the interior portion of the base material is impregnated with the bioprotectant. In some embodiments, at least 50% of the interior portion of the base material is impregnated with the bioprotectant. In some embodiments, at least 60% of the interior portion of the base material is impregnated with the bioprotectant. In some embodiments, at least 70% of the interior portion of the base material is impregnated with the bioprotectant.

In some embodiments, the method further comprising forming a medical implant with the medical implant composition, wherein the composition is present in, and provides structural strength to, the medical implant. In some embodiments, the medical implant is selected from the group consisting of a surgical mesh, a breast augmentation implant, a cannula, a catheter, an orthopedic implant, or a hernia repair implant. In some embodiments, the medical implant is a surgical mesh. In some embodiments, the surgical mesh is a synthetic mesh, an acellular mesh, or a hybrid mesh comprising an acellular mesh and a synthetic mesh. In some embodiments, the medical implant is a breast augmentation implant.

The method disclosed herein can be extended from the medical implant material impregnated with bioprotectant to medical implant material impregnated other pharmaceutical agents in some embodiments.

DETAILED DESCRIPTION

Figure 1:
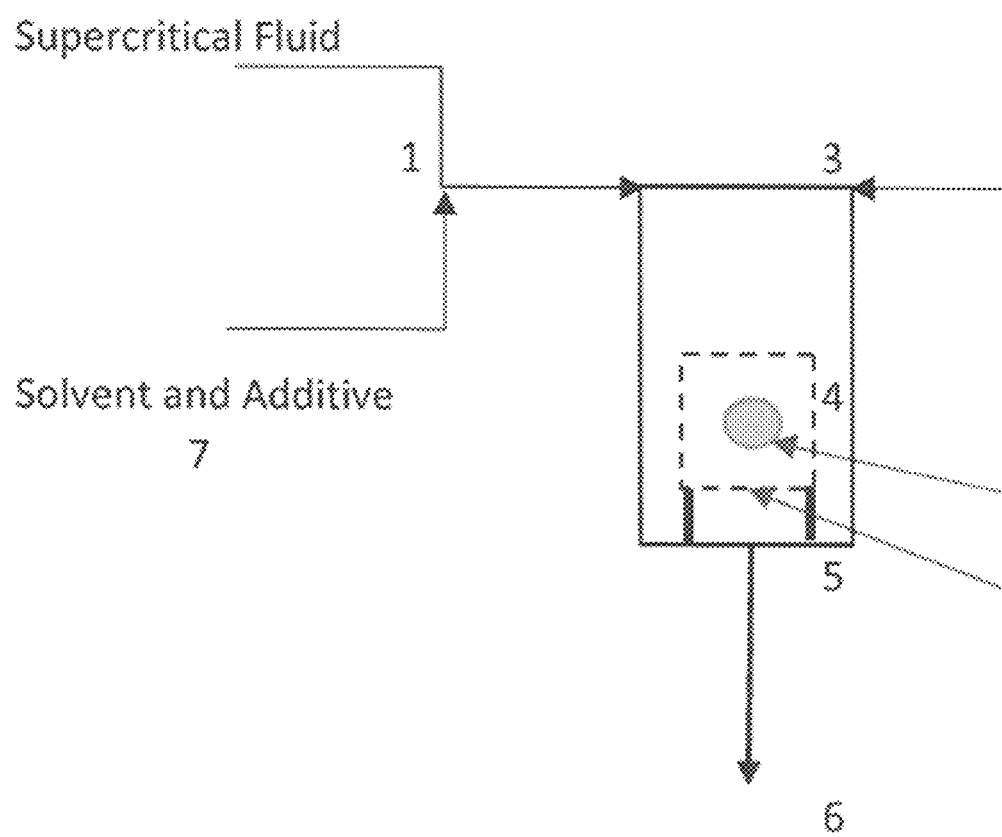
FIG. 1 schematically illustrates a non-limiting embodiment of the method according to the present disclosure. In this embodiment, supercritical fluid (1) was combined with the bioprotectant ("additive") and optional solvent before flowing into the enclosure (3). The enclosure may have a meshed cage (5) supporting the base material (5) therein. After the bioprotectant is infused in or impregnated in the base material, pressure is released through port (6)
Figure 2:
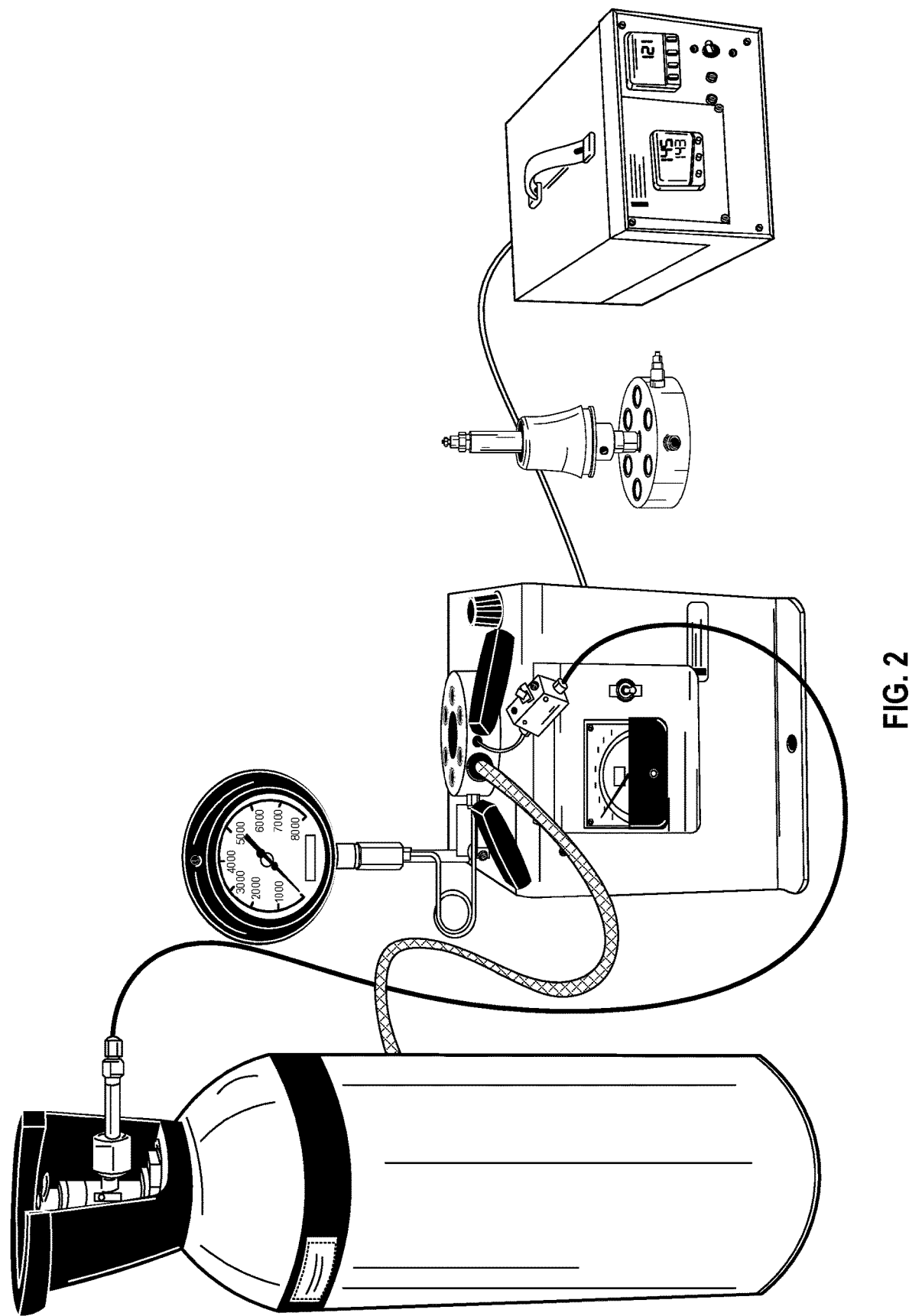
FIG. 2 is a photograph of a non-limiting embodiment of the process equipment assembly, showing the supercritical carbon dioxide source (cylinder), enclosure with pressure gauge autoclave, and heating controller/temperature gauge (at the far right)
Figure 3:
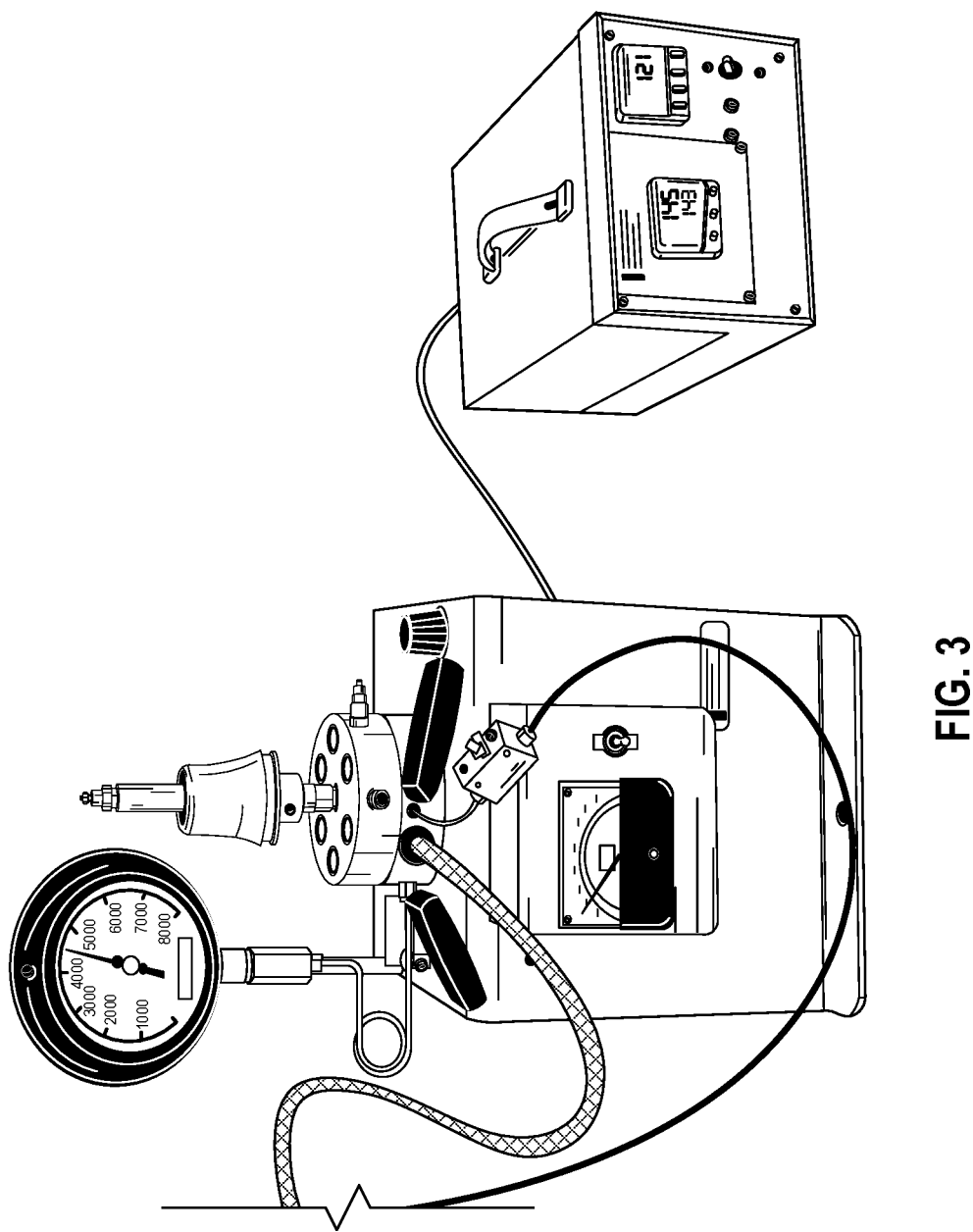
FIG. 3 is a photograph of the process equipment assembly of FIG. 2 in operation.
Figure 4:
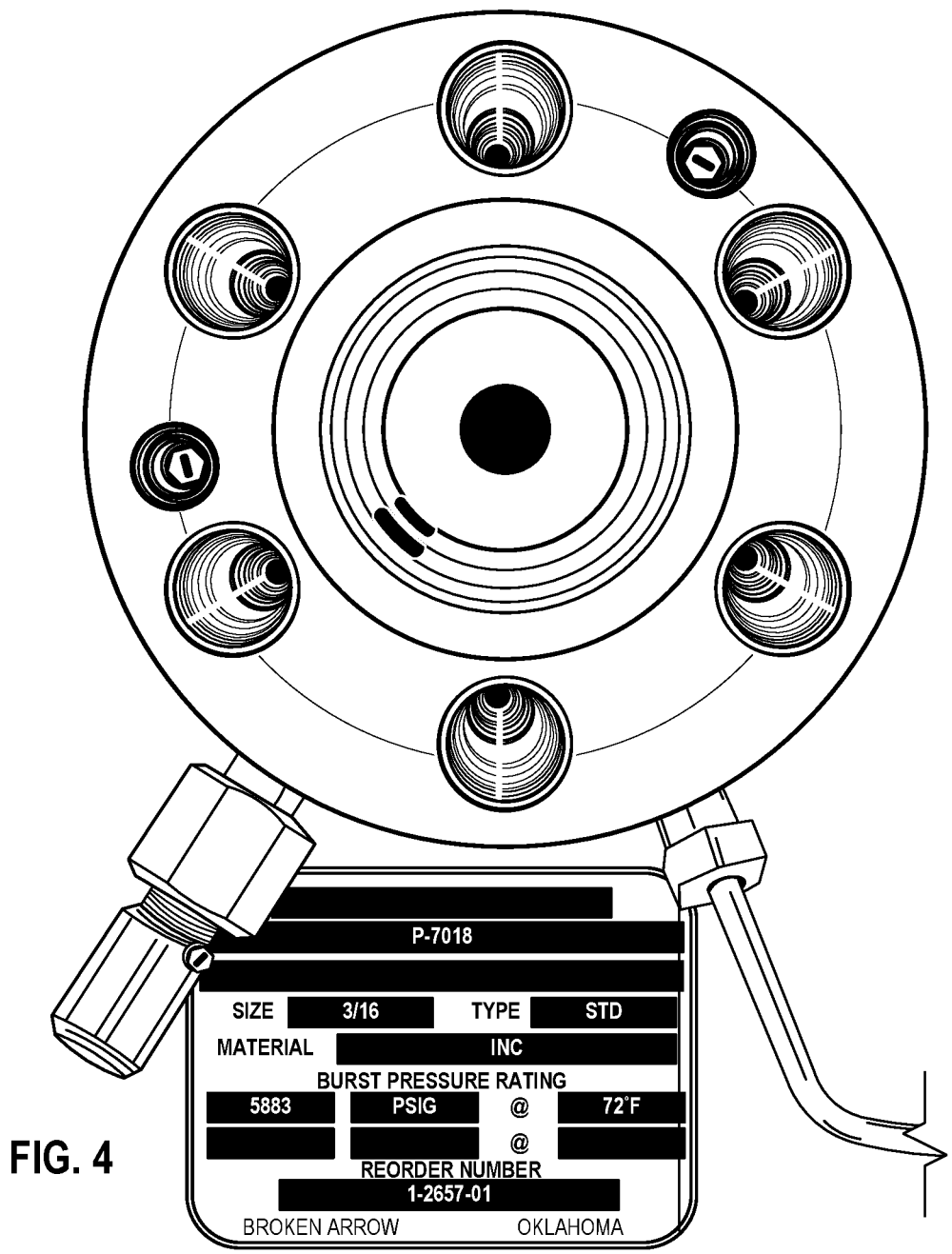
FIG. 4 is photograph of the enclosure (top view)
Figure 5:
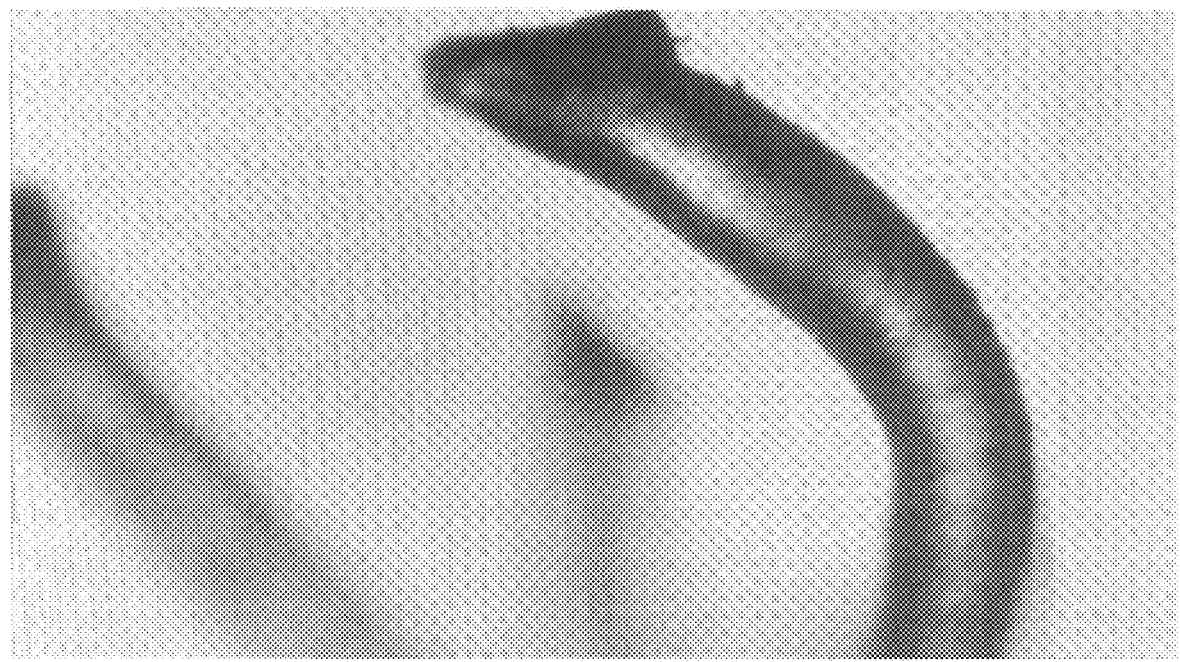
FIG. 5 is a microscopic view of a mesh implant impregnated with a dark textile dye and an optional bioprotectant using the process disclosed herein. After immersing in 70% ethanol for three days and washing with water for three times, the interior of the mesh material is still substantially impregnated with the dye.
Figure 6:
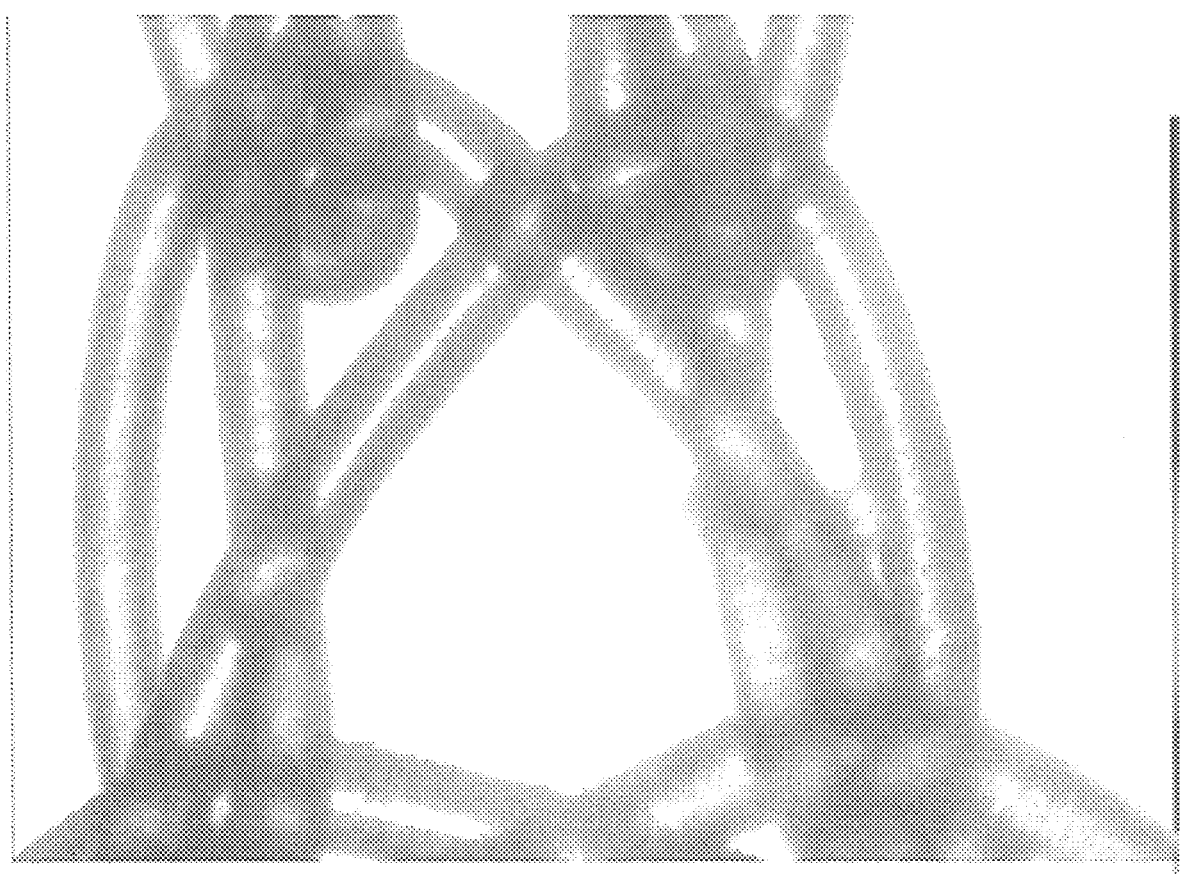
FIG. 6 is a microscopic view of a mesh implant impregnated with a dark textile dye and an optional bioprotectant using the process disclosed herein. After immersing in 70% ethanol for three days and washing with water for three times, the interior of the mesh material is still substantially impregnated with the dye (e.g. at least 30%, 50%, 60%, or 70% of the interior of the mesh material impregnated with the dye)
Figure 7:
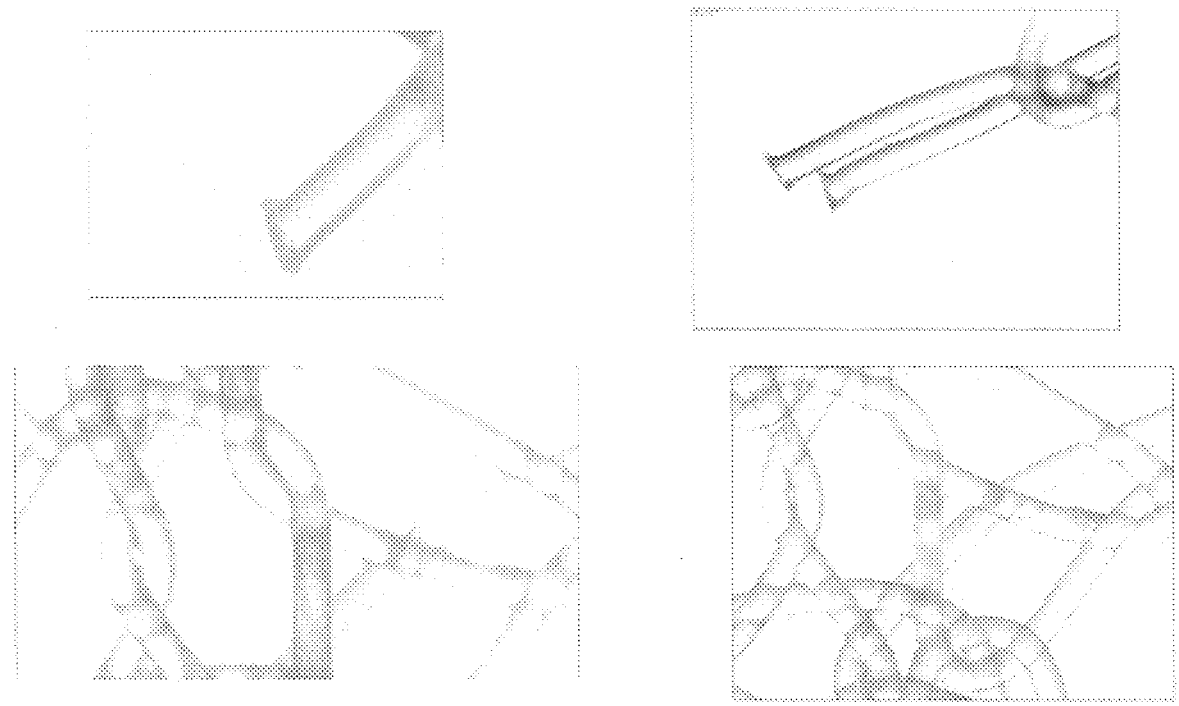
FIG. 7 is a microscopic view of a control mesh implant solution-coated with a dark textile dye and an optional bioprotectant by incubating the mesh material in a solution of the dark textile dye and optional bioprotectant for 24 hours. After immersing in 70% ethanol for three days and washing with water for three times, only limited amount of the dye remains with the mesh material, and most present on the surface of the mesh material.
Figure 8:
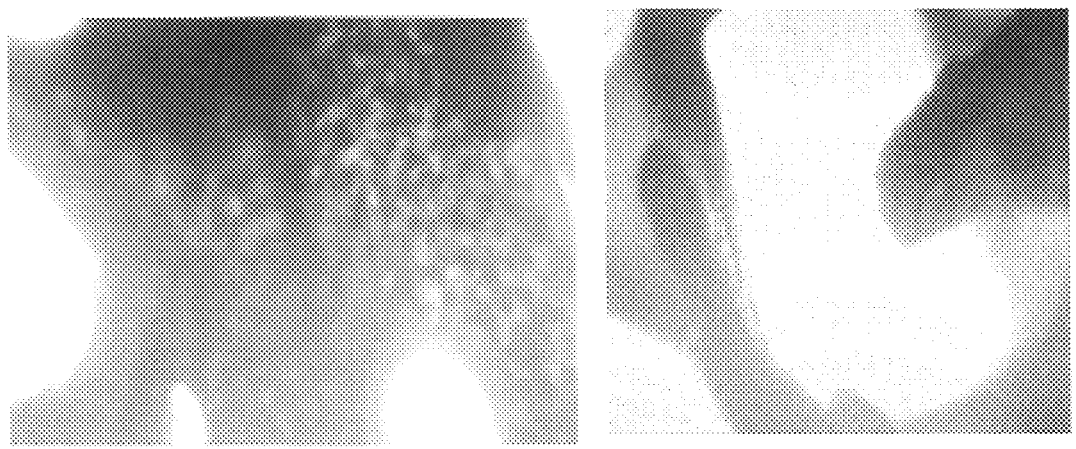
FIG. 8 is a microscopic view of a human bone graft material impregnated with a dark textile dye and an optional bioprotectant using the process disclosed herein. After immersing in 70% ethanol for three days and washing with water for three times, the interior of the mesh material is still substantially impregnated with the dye.
Figure 9:
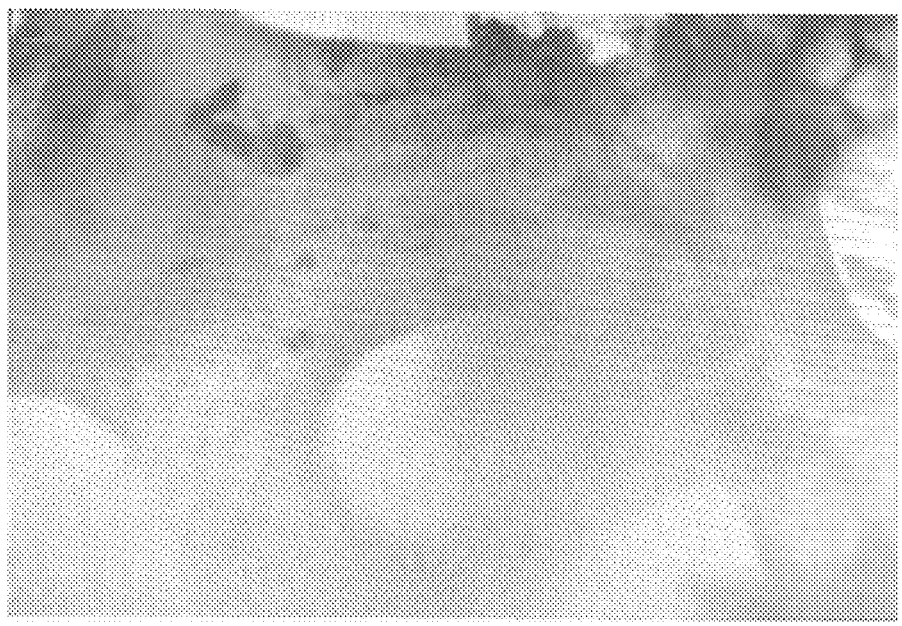
FIG. 9 is a microscopic view of a human bone graft material solution-coated with a dark textile dye and an optional bioprotectant by incubating the mesh material in a solution of the dark textile dye and optional bioprotectant for 24 hours. After immersing in 70% ethanol for three days and washing with water for three times, the interior of the mesh material retains little or no dye.
Figure 10:
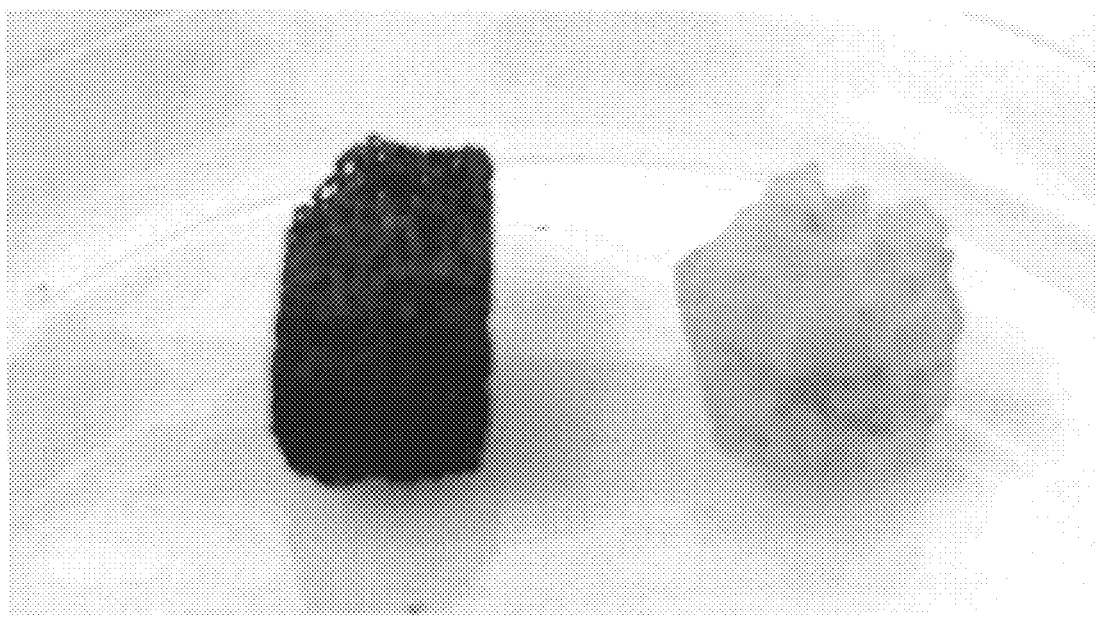
FIG. 10 is a photograph of the human bone graft material impregnated with a dark textile dye and an optional bioprotectant in FIG. 8 and the control human bone graft material solution-coated with the dark textile dye and an optional bioprotectant in FIG. 9. After immersing in 70% ethanol for three days and washing with water for three times, the interior of the mesh material is still substantially impregnated with the dye, the SCF-processed bone graft material still retain substantial amount of the dye, while the solution-coated bone graft material retain little or no dye.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Drug/polymer composite materials may be formed either by solvent-based processing where a solvent or combination of solvents is used to facilitate intimate mixing of the drug with polymer(s) by a combination of reducing the polymer viscosity and by dispersing/dissolving the drug into a fluid-like phase or by processing a mixture of drug(s)—polymer(s) at an elevated temperature sufficient to cause flow of the polymer into a desired shape. The solvents commonly utilized include all common organic solvents, halogenated solvents and aqueous solvent compositions. However, solvent-based processing can adversely affect the drug by reacting, bonding, or binding with the chemical functionality of many drugs. In addition, removal of solvent and solvent residues from the composite material is problematic and requires extensive processing with heat, vacuum, etc. Further, these processes can be process/cost intensive, lack precise material control, and can adversely affect the drug or active pharmaceutical ingredient (API). For example: (i) Trace solvent residues are unavoidable and are often toxic or can negatively interact with the drug or polymer molecules altering the therapeutic effect; and (ii) Solvent-based processing can also adversely affect the primary structure of the drug in the polymer matrix. The present disclosure recognizes the need for new approaches to the production of drug/polymer composite materials, and for new materials produced by such methods.

Certain Definitions

Subjects that may be treated by the present invention include both human subjects for medical purposes and animal subjects for veterinary and drug screening and development purposes. Other suitable animal subjects are, in general, mammalian subjects such as primates, bovines, ovines, caprines, porcines, equines, felines, canines, rodents (e.g., rats and mice), etc. Human subjects are the most preferred. Human subjects include fetal, neonatal, infant, juvenile and adult subjects.

Shaped articles as used herein include, but are not limited to, pills, tablets, drug depots or drug delivery devices (e.g., subcutaneous implants), biomedical implants, etc.

"Biomedical implant" as used herein includes but is not limited to drug depots and drug delivery devices, stents (e.g., vascular stents), electrodes, catheters, leads, implantable pacemaker or cardioverter housings, joints, screws, rods, ophthalmic implants (including, but not limited to, intraocular lens implants, glaucoma implants or drainage implants, and punctal implants or plugs), etc. The implants may be of any suitable material, including but not limited to organic polymers (including stable or inert polymers and polymers), metals such as stainless steel and titanium, inorganic materials such as silicon, and composites thereof.

"Drug depot" or "drug delivery device" include those be configured for any route of administration, including those that may be implanted (luminal, venous, subcutaneous, muscular, ocular), inserted (oral, rectal, vaginal, ocular) or topically applied (transdermal, transmucual, sublingual).

"Treat" as used herein refers to any type of treatment or prevention that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc. As such, the term "treatment" also includes prophylactic treatment of the subject to prevent the onset of symptoms. As used herein, "treatment" and "prevention" are not necessarily meant to imply cure or complete abolition of symptoms." to any type of treatment that imparts a benefit to a patient afflicted with a disease, including improvement in the condition of the patient (e.g., in one or more symptoms), delay in the progression of the disease, etc.

"Pharmaceutical excipient" as used herein includes refers to any pharmaceutically acceptable material that is included in a drug composition to enhance the pharmaceutical (including manufacturing and shelf-stability) and/or pharmacological properties thereof. Pharmaceutical excipients include, but are not limited to, adjuvants, surfactants, stabilizers, morphology modifiers, porogens, diluents, carriers, solubilizers, antioxidants, lubricants (or glidants), binders, disintegrants, and mixtures thereof.

As used in the present specification, the following words and phrases are generally intended to have the meanings as set forth below, except to the extent that the context in which they are used indicates otherwise.

"Base material" as used herein, refers to any natural, naturally derived, processed, or synthetic material that forms the structural base of a medical implant or medical implant. As used herein, "base material" can be a reference to the chemical substances, or it can be a reference to the three-dimensional member formed by the chemical substances, in which case the base material will have a surface portion and interior portion.

The implants may be formed from any suitable material, including but not limited to organic polymers (including stable or inert polymers and biodegradable polymers), metals, inorganic materials such as silicon, and composites thereof, including layered structures with a core of one material and one or more coatings of a different material.

In some embodiments, the biomedical implant is an expandable intraluminal vascular graft or stent (e.g., comprising a wire mesh tube) that can be expanded within a blood vessel by an angioplasty balloon associated with a catheter to dilate and expand the lumen of a blood vessel, such as described in U.S. Pat. No. 4,733,665 to Palmaz Shaz.

"Pharmaceutical agent" or "active pharmaceutical ingredient" as used herein refers to any of a variety of drugs or pharmaceutical compounds that can be used as active agents to prevent or treat a disease or infection (meaning any treatment of a disease in a mammal, including preventing the disease, i.e. causing the clinical symptoms of the disease not to develop; inhibiting the disease, i.e. arresting the development of clinical symptoms; and/or relieving the disease or infection, i.e. causing the regression of clinical symptoms). It is possible that the pharmaceutical agents of the invention may also comprise two or more drugs or pharmaceutical compounds. Pharmaceutical agents, include but are not limited to antiiinfective agents, antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti-Parkinson's agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal antiinflammatory drugs {NSAIDs], cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenytoin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotipine and the like.

The active ingredients may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereomers.

As used herein, the term "antimicrobial agent" refers to compounds that inhibit the growth, proliferation, or multiplication of microbes, or that kill microbes. Suitable "antimicrobial agents" are antibacterial agents (effective against bacteria), antiviral agents (effective against viruses), antifungal agents (effective against fungi), antiprotozoal (effective against protozoa), and/or antiparasitic to any class of microbial parasites. "Antimicrobial agents" may work by any suitable mechanism against the microbes, including by being toxic or cytostatic.

"Active biological agent" as used herein refers to a substance, originally produced by living organisms, that can be used to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the active biological agents of the invention may also comprise two or more active biological agents or an active biological agent combined with a pharmaceutical agent, a stabilizing agent or chemical or biological entity. Although the active biological agent may have been originally produced by living organisms, those of the present invention may also have been synthetically prepared, or by methods combining biological isolation and synthetic modification. By way of a non-limiting example, a nucleic acid could be isolated form from a biological source, or prepared by traditional techniques, known to those skilled in the art of nucleic acid synthesis. Furthermore, the nucleic acid may be further modified to contain non-naturally occurring moieties. Non-limiting examples of active biological agents include peptides, proteins, enzymes, glycoproteins, nucleic acids (including deoxyribonucleotide or ribonucleotide polymers in either single or double stranded form, and unless otherwise limited, encompasses known analogues of natural nucleotides that hybridize to nucleic acids in a manner similar to naturally occurring nucleotides), antisense nucleic acids, fatty acids, antimicrobials, vitamins, hormones, steroids, lipids, polysaccharides, carbohydrates and the like. They further include, but are not limited to, antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals and chemotherapeutic agents. Preferably, the active biological agent is a peptide, protein or enzyme, including derivatives and analogs of natural peptides, proteins and enzymes.

"Activity" as used herein refers to the ability of a pharmaceutical or active biological agent to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Thus, the activity of a pharmaceutical or active biological agent should be of therapeutic or prophylactic value.

"Secondary, tertiary and quaternary structure" as used herein are defined as follows. The bioprotectant in some embodiments may possess some degree of secondary, tertiary and/or quaternary structure, upon which the activity of the agent depends. As an illustrative, non-limiting example, proteins possess secondary, tertiary and quaternary structure. Secondary structure refers to the spatial arrangement of amino acid residues that are near one another in the linear sequence. The α-helix and the β-strand are elements of secondary structure. Tertiary structure refers to the spatial arrangement of amino acid residues that are far apart in the linear sequence and to the pattern of disulfide bonds. Proteins containing more than one polypeptide chain exhibit an additional level of structural organization. Each polypeptide chain in such a protein is called a subunit. Quaternary structure refers to the spatial arrangement of subunits and the nature of their contacts. For example, hemoglobin consists of two a and two p chains. It is well known that protein function arises from its conformation or three-dimensional arrangement of atoms. One aspect of the present invention is to manipulate active biological agents, while being careful to maintain their conformation, so as not to lose their therapeutic activity.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide the polymer part of the composite materials of the invention including plasticized polymers that form a matrix with interstices wherein the drugs are sequestered. In addition to their role in forming the matrices of the invention, the polymers can be used as coating for composite materials of the invention. Selection of appropriate polymers can be employed in forming composite materials with differing properties. Those of skill in the art of polymer chemistry will be familiar with the different properties of polymeric compounds. "Polymer" as used herein refers to organic polymers, and includes copolymers of a named polymer with other constituents. In some embodiments, such as in the preparation of drug depots or drug delivery devices, the polymer is preferably an absorbable and/or resorbable polymer. In other embodiments the polymer is preferably non-resorbable and biocompatible. Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, polyurethanes, polystyrenes, copolymers, silicones, polyorthoesters, polyanhydrides, copolymers of vinyl monomers, polycarbonates, polyethylenes, polypropylenes, polylactic acids, polyglycolic acids, polycaprolactones, polyhydroxybutyrate valerates, polyacrylamides, polyethers, polyurethane dispersions, polyacrylates, acrylic latex dispersions, polyacrylic acid, mixtures and copolymers thereof. The polymers of the present invention may be natural or synthetic in origin, including gelatin, chitosan, dextrin, cyclodextrin, Poly(urethanes), Poly(siloxanes) or silicones, Poly(acrylates) such as poly(methyl methacrylate), poly(butyl methacrylate), and Poly(2-hydroxy ethyl methacrylate), Poly(vinyl alcohol) Poly(olefins) such as poly(ethylene), poly(isoprene), halogenated polymers such as Poly(tetrafluoroethylene)—and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc. Suitable polymers also include absorbable and/or resorbable polymers including the following, combinations, copolymers and derivatives of the following: Polylactides (PLA), Polyglycolides (PGA), Poly(lactide-co-glycolides) (PLGA), Polyanhydrides, Polyorthoesters, Poly(N-(2-hydroxypropyl) methacrylamide), Poly(1-aspartamide), etc.

Any suitable polymer can preferably be used to carry out the present invention, including but not limited to: natural and synthetic polymers, gelatin, chitosan, dextrin, cyclodextrin, Poly(urethanes), Poly(siloxanes) or silicones, Poly(acrylates) such as poly(methyl methacrylate), poly(butyl methacrylate), and Poly(2-hydroxy ethyl methacrylate), Poly(vinyl alcohol) Poly(olefins) such as poly(ethylene), poly(isoprene), halogenated polymers such as Poly(tetrafluoroethylene)—and derivatives and copolymers such as those commonly sold as Teflon® products, Poly(vinylidine fluoride), Poly(vinyl acetate), Poly(vinyl pyrrolidone). Poly(acrylic acid), Polyacrylamide, Poly(ethylene-co-vinyl acetate), Poly(ethylene glycol), Poly(propylene glycol), Poly(methacrylic acid); etc. Suitable polymers also include absorbable and/or resorbable polymers including the following, combinations, copolymers and derivatives of the following: Polylactides (PLA), Polyglycolides (PGA), Poly(lactide-co-glycolides) (PLGA), Polyanhydrides, Polyorthoesters, Poly(N-(2-hydroxypropyl) methacrylamide), Poly(1-aspartamide), etc.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life, increased in vivo stability, good biocompatibility, good bioavailability or modified release rates. Typically, for the present invention, the desired morphology of a pharmaceutical agent would be crystalline or semi-crystalline, although this may vary widely depending on many factors including, but not limited to, the nature of the pharmaceutical agent, the disease to be treated/prevented, the intended storage conditions for the substrate prior to use or the location within the body of any biomedical implant. In some embodiments, at least 10%, 20%, 30%, 40%, 50%, 60%, 70%, 80%, 90% or 100% of the pharmaceutical agent is in crystalline or semi-crystalline form.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts.

"Supercritical fluid", "near-critical fluid", "critical fluid", "densified fluid" or "densified gas" as used herein refers to a substance under pressure greater than ambient conditions, where it demonstrates a density greater than 0.4 g/cc but the mobility of a gas, i.e. a gas with liquid-like densities in which the pressure and temperature are above the critical point (the temperature and pressure at which the density of the liquid and vapor phases become identical). Examples of near critical fluids include fluids which are in gaseous state at standard temperature and pressure (STP) conditions and have a critical density above 0.2 g/cc. See, e.g., U.S. Pat. Nos. 6,860,123; 6,837,611; and 6,755,871. Examples of substances that demonstrate supercritical or near critical behavior suitable for the present invention include, but are not limited to carbon dioxide, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfuoropropane, chloroform, trichloro-fluoromethane, dichloro-difluoromethane, dichloro-tetrafluoroethane) and mixtures thereof. Carbon dioxide is preferred. For densified carbon dioxide, conditions including a temperature between 0° C. and 100° C. and a pressure between 30 psig and 10,000 psig are preferred.

"Enclosure" as used herein refers to a vessel that can be sealed from the outside atmosphere, and thus may be at significantly different temperatures and pressures to the outside atmosphere.

The terms "effective amount" or "therapeutically effective amount," as used herein, refer to a sufficient amount of the bioprotectant being released from the implant material that would be expected to relieve to some extent one or more of the symptoms of the disease or condition being treated. For example, the result of release of the bioprotectant from the implant material disclosed herein is reduction and/or alleviation of the signs, symptoms, or causes of infection. For example, an "effective amount" for therapeutic uses is the amount of the bioprotectant, including a formulation as disclosed herein required to provide a decrease or amelioration in disease symptoms without undue adverse side effects. The term "therapeutically effective amount" includes, for example, a prophylactically effective amount. An "effective amount" of a bioprotectant released from the implant material disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate-release dosing format based upon pharmacokinetic and pharmacodynamic considerations.

The terms "enhance" or "enhancing" refers to an increase or prolongation of either the potency or duration of a desired effect of the bioprotectant, or a diminution of any adverse symptomatology. For example, in reference to enhancing the effect of the bioprotectant disclosed herein, the term "enhancing" refers to the ability to increase or prolong, either in potency or duration, the effect of other therapeutic agents that are used in combination with the bioprotectant disclosed herein. An "enhancing-effective amount," as used herein, refers to an amount of the bioprotectant or other therapeutic agent that is adequate to enhance the effect of another therapeutic agent or bioprotectant in a desired system. When used in a patient, amounts effective for this use will depend on the severity and course of the disease, disorder or condition, previous therapy, the patient's health status and response to the drugs, and the judgment of the treating physician.

Base Material

In some embodiments, the medical device is made of any biocompatible material suitable for medical devices. In some embodiments, the biocompatible material includes without limitation natural polymers, synthetic polymers, ceramics, and metals. In some embodiments, the medical device comprises one material. In some embodiments, the medical device comprises a plurality of materials. In some embodiments, the medical device has a surface comprising one or more materials.

In some embodiments, the surface of the medical device comprises polyvinyl chloride, polyethylene, polyurethane, latex, silicone, polytetrafluoroethylene, stainless steel, titanium, metals, poly(methyl methacrylate), acrylic, ceramic, bioactive glass, nitinol, biocompatible polymer, biocompatible biomaterials, or combinations thereof.

In some embodiments, the surface or other portions of the medical device comprises metals and alloys based on titanium (such as nitinol, nickel titanium alloys, thermo-memory alloy materials), stainless steel, tantalum, nickel-chrome, or certain cobalt alloys including cobalt-chromium-nickel alloys, or combinations thereof. In some embodiments, the medical implants comprises solid metals, for example, gold, silver, stainless steel, platinum, palladium, iridium, iron, nickel, copper, titanium, aluminum, chromium, cobalt, molybdenum, vanadium, tantalum, and alloys thereof. In some embodiments, the medical implant comprises a polymer, such as polyethylene, or a ceramic.

In some embodiments, the medical device comprises polymer(s) that are biocompatible and avoid irritation to body tissue. In some embodiments, the polymers are biostable or bioabsorbable. In some embodiments, the surface or other portions of the medical device comprises without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins, or combinations thereof. In some embodiments, the surface or other portions of the medical device includes without limitation dacron polyester, poly(ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), polytetrafluoroethylene poly(HEMA), polyhydroxyalkanoates, polytetrafluoroethylene, polycarbonate, poly(glycolide-lactide) co-polymer, polylactic acid, poly(ε-caprolactone), poly(β-hydroxybutyrate), polydioxanone, poly(γ-ethyl glutamate), polyiminocarbonates, poly(ortho ester), polyanhydrides, alginate, dextran, cotton, polyglycolic acid, polyurethane, or derivatized versions thereof, or combinations thereof.

In some embodiments, the materials are made into elongated members or wire-like elements and then woven to form a mesh network. In some embodiments, polymer filaments are also used together with the metallic elongated members or wire-like elements to form a network mesh. In some embodiments, a mesh network made of metal is welded, twisted, bent, glued, tied (with suture), heat sealed to one another; or connected in any manner known in the art.

In some embodiments, the surfaces of the medical implant are textured. In some embodiments, the textured surfaces enable the anti-microbial coating to be applied to the medical implant. The medical implant surface is textured uniformly with surface irregularities, including pores (micropores), dimples, spikes, ridges, grooves (e.g., microgrooves), roughened texture (e.g., microtextured), surface grain, strips, ribs, channels, ruts. The size of the micropores, dimples, spikes, ridges, grooves (e.g., microgrooves), roughened texture (e.g., microtextured), surface grain, strips, ribs, channels, ruts can range from about 1 μm to about 2000 μm. In some embodiments, the size ranges from about 10 μm to about 100 μm. In some embodiments, implant surface has pores from about 200 μm to about 2000 μm.

Mesh Implant Material

Implants are frequently used in modern surgical procedures to reinforce or augment native tissues. Medical implants are available in a wide variety of materials and a diverse range of applications; however, all implanted materials carry the risk of infection. Depending on the selection of material, there may be chronic inflammation caused by immune reaction to the non-native material. Use of biologic material, whether a decellularized donor tissue or a biosynthetic material of biochemical which can be degraded by metabolism, offer less immune reaction but still have risk of infection. Medical implants are particularly employed in ventral abdominal hernia repair. Evidence shows mesh support repair performs far better than suture closure; loss of native tissue integrity due to aging, obesity, diabetes, immune suppression treatment requires support for strength of repair. Unfortunately, infection of ventral hernia mesh repair is a common occurrence, the incidence may be 30% or more of mesh repairs. Mesh infection is costly to correct and associated with significant patient morbidity. Hernia medical implants (generically, termed mesh) have undergone several evolutions of design from synthetic plastic polymer woven meshes to decellularized biologic materials and biosynthesized biologic materials and hybrid grafts incorporating both synthetic and biologic materials. All current classes of mesh in clinical marketplace have significant deficiencies in outcome performance in one or more areas (see Table 1). Decellularized biologic mesh (acellular scaffold graft) provides the best outcome when tissue regeneration occurs, but infection risk still exists without protection of antimicrobial/antibiofilm agents incorporated into mesh. In addition, the costs of decellularization is very high and increases healthcare to prohibitive levels, cost of the graft is a limitation in utilization by surgeons.

TABLE 1

| Class of Mesh | Material | Pros | Cons |
| --- | --- | --- | --- |
| Synthetic | Plastics, polypropylene, polyester, PTFE, etc. | High Mechanical Strength - long term endurance after implantation | High Risk for infection (many require removal to treat infection), chronic inflammation, inelastic abdominal wall, chronic pain |
| Biological Acellular Scaffold Graft | Decellularized tissue from animal or human sources | Lower risk of infection, Low Immune Reaction, Healing/ remodeling of tissue to regenerate architecture of abdominal wall. | Low Mechanical Strength - frequent hernia recurrence (even without infection) Do not have anti-infective or anti-biofilm properties |
| Biosynthetic mesh | Polymers of biochemical composition (polyactate, etc.) | Resorbed by natural metabolic activity, Lower Risk of infection and inflammation | Low Mechanical Strength - Resorbed by body in advance of complete healing with hernia recurrence (even without infection) |

TABLE 1-continued

| Class of Mesh | Material | Pros | Cons |
| --- | --- | --- | --- |
| Hybrid mesh | Plastic synthetic covered by biosynthetic cover | Lower Risk of Infection but high risk if surface is resorbed early | Problems of Synthetic Mesh with High Risk of Infection & Inflammation if surface is resorbed |
| Impregnated Mesh (NEW Class) | Base material, synthetic or biological which has an impregnated matric with antimicorbial - antibiofilm compounds (Super Critical Fluid Process) | Synthetic of a synthetic with Low Risk for infection. (A decellularized scaffold graft can be selected if preferred and treated with antimicrobial & antibiofilm agents) | Premarket status |

Synthetic meshes have superior mechanical strength and are resistant to breakdown by body defenses, but are associated with high rates of infection which requires intense treatment (with possible reoperation to remove implant and correct defect) in 15% to 30% of cases. Biologic meshes have improved outcomes for potentially infected repairs (wound contamination operations, Grade 3-4) but do not have the mechanical strength capacity of synthetic mesh resulting in frequent hernia recurrence despite no infection present (48% Rosen). Biologic meshes are labor intensive to mass produce, contributing an extreme additional cost to healthcare, often doubling or tripling cost of repairs. Biosynthetic biologic meshes may exhibit recurrence due to resorption prior to complete healing. Hybrid meshes compromised of synthetic cores with biologic surfaces have not been evaluated for sufficient trial length to ascertain the long-term outcomes concerning infection and hernia recurrence, however the cost of production and subsequent charge to healthcare is significant and are a less than ideal solution.

Therefore, a lower cost and efficient means of converting strong mesh material into low risk-for-infection characteristics is highly desired for current surgical practice. Prior attempts to coat synthetics with antimicrobials or antibiofilm agents have employed complex and expensive multistep processes and utilized toxic solvents as a part of the process. In short, mesh repair of ventral hernia is currently unsatisfactory with significant failures either due to infection or mechanical failure despite numerous modifications of mesh material employed and great increases production complexity and cost of meshes. A mechanically strong and anti-infective material that is not prohibitive in cost is a high priority goal for general and plastic surgery.

Biology of Mesh Implant Failure

In surgical repair of hernias, use of supportive materials to reinforce inadequate native tissue is a common procedure. Any material implanted into the body will undergo recognition and response by the immune system. The "foreign body response" refers to reaction to materials characterized as "non-self" (foreign) by immune defense mechanisms. There are multiple processes involved in this activity including recognition of foreign material by cellular immune mechanisms and biochemical inflammatory responses. These processes serve to activate and recruit specialized immune cells responses which act on the material to neutralize, degrade, and remove from the body.

This scenario is commonly encountered in a contaminated wound. The contaminants are engulfed, sequestered, and removed by immune cells (white blood cells). This elegant process utilizes chemical signals to increase blood flow and blood vessel permeability in the local area to deliver recruited immune cells; components of the inflammatory response. The successful inflammatory response serves to clean and clear an injured tissue and stimulate blood supply and tissue regeneration, i.e., the healing process.

If a sufficient number of reproducing microbes (bacteria in particular) are present in a contaminated wound, they may outgrow the defensive actions of the immune response and develop a population of microbes residing in a network adhering to surfaces, termed a biofilm, and pose an additional barrier to immune defense. This complex of bacterial growth in the presence of immune attack is the core of wound infection. The presence of the biologically inert synthetic mesh is detrimental since it has no innate anti-infective capability to discourage bacterial growth and biofilm formation, thus serving as a nidus of local infection, bacterial contamination occurs. In addition, synthetic materials do not become vascularized in the same manner as biologic material which stimulate new blood vessel in-growth (angiogenesis) and present areas of isolation from adequate delivery of immune cells to clear infection.

Sometimes pure synthetic mesh implants can develop chronic infection as a continuous foreign body reaction along with creating persistent inflammatory conditions which delay and inhibit complete healing. Biologic mesh materials allow bacterial penetration into their interior which is of significant concern (Hernia (2015) 19:965-973)

Recognizing the incapacity of all variants of synthetic mesh to promote regeneration and associated higher infection with hernia failure, attempts to utilize biologic material to stimulate tissue and blood vessel regeneration have been employed. Indeed, biologic meshes do perform much better in potentially infective hernia repairs but they do not possess the native mechanical strength required to resist the stress forces encountered by extreme motion of the abdominal wall, as in cough, Va Isa Iva maneuver, rapid torso rotation, etc. Evaluations of biologic mesh in ventral hernia repair has shown the infection rate to be significantly lower in contaminated scenarios but the long term mechanical failure with hernia recurrence may be very high (48% Rosen). In the process of biologic mesh implantation, there is tissue regeneration accompanied by resorption of the biologic implanted material. If the resorption of implanted mesh occurs before complete tissue regeneration, then inadequate tissue resilience and mechanical strength may result with failure of hernia repair under ordinary stress forces generated at the abdominal wall; often the case for biosynthetic biologic meshes. Thus, biologic meshes, despite lowered infection rates, provide an inadequate solution to ventral hernia repair. Both decellularized tissue from non-human (xenograft) and human (allograft) origins have been employed in a class of biologic implants, both exhibiting the strength inadequacies outlined above. A different biologic mesh strategy (biosynthetic mesh) incorporates "naturally occurring biochemical" compounds in mesh manufacture that produce a biocompatible material that is resorbed by chemical breakdown into non-toxic elemental components by the body's metabolism. An example is use of a polymer made of lactic acid, a naturally occurring biochemical compound, which is eventually reduced to carbon and water. However, resorption of such biologic material is uncontrolled and cannot be predicted in individual cases, therefore a significant number will be degraded and resorbed prior to complete healing with resulting weakened repair and hernia recurrence. Hybrid meshes are composed of synthetic material cores with biologic material surfaces have been introduced to surgical practice, but long-term results have not been demonstrated as yet; in any event production of hybrid meshes is complex and increase in healthcare costs are significant.

Significant local infection may develop when bacteria are encountered, either from wound contamination or through hematogenous spread, and are not successfully eliminated by immune mechanisms. Medical implants possess no innate antimicrobial activity, may be poorly vascularized, and may possess proinflammatory characteristics; thus, bacteria may have a favored site to form a conglomerate network known as a biofilm. The biofilm complex creates a matrix which has increased resistance to immune attack and antibiotic treatment resulting in the difficult-to-treat surgical infections often encountered with implants. In the presence of such an infection, local native tissue breaks down from inflammatory chemical & enzymatic degradation and may result in disruption of wound with hernia recurrence. Treatment is by drainage and antimicrobial therapy and often requires reoperation—complications with significant expense and considerable morbidity and potential mortality. Therefore, deterrence of biofilm formation is a major goal in implant product future design.

The use of anti-biofilm compounds (ABC's) both on the surface and in the matrix of medical implants is a highly desired improvement to provide implant resistance to infection. Some surgical biologic mesh products (porcine dermis derived) have antimicrobial surface coatings applied, but they are exterior to the mesh body matrix so that bacterial invasion of an interior space through an opening or defect created by a suture passage may set up biofilm production leading to persistent infection; in short, they are not robustly protected against biofilm formation and are subject to the erosive and degrading forces of the innate immune response and inflammation mechanisms.

Current manufacture of synthetic medical implants requires methods which are incompatible with stability of ABC chemicals or other Active Pharmaceutical Ingredients, such as hot melt-extrusion or solvent casting processes, therefore a separate method of complete impregnation of the implant material with intact target compound conservation is highly desired. By this transformation, the implant material becomes a significant barrier to biofilm formation throughout its matrix. Complete impregnation is essential in implantation in vivo as physiologic immune reactions to any substance will include a variety of biochemical and cellular processes which are likely to degrade and expose any implant material to the recipient organism. Such an unprotected submicroscopic cavity with poor penetration by immune cells and insufficient delivery of antibiotic drugs could create "nook" where bacteria could gain a beachhead by biofilm formation leading to growing infection and implant expulsion—if that implant was not impregnated through-and-through with Anti-Biofilm Compounds (ABCs) to defeat colonization. Thus, complete impregnation of ABC is essential to not allow a nidus where bacteria can gain purchase and begin biofilm formation at an unprotected site. The invention provides a process whereby biologic material (such as porcine tissue) can be decellularized in a single step by the super critical fluid method and implant material (either biologic or synthetic) can be impregnated with a selected agent or group of agents to provide bioprotective capabilities to improve performance and outcomes.

Bioprotectant

A wide variety of bioprotectant can be incorporated into the base material using the supercritical fluid infusion/ impregnation method disclosed herein. In some embodiments, the bioprotectant is an immunosuppressant agent or an anti-infective agent. In some embodiments, the anti-infective agent is an anti-microbial agent, an anti-biofilm agent, or a combination thereof.

Antimicrobial Agents

Any antimicrobial agent useful for the treatment of otic disorders, e.g., inflammatory diseases or infections of the ear, is suitable for use in the formulations and methods disclosed herein. In some embodiments, the antimicrobial agent is an antibacterial agent, an antifungal agent, an antiviral agent, an antiprotozoal agent, and/or an antiparasitic agent. Antimicrobial agents include agents that act to inhibit or eradicate microbes, including bacteria, fungi, viruses, protozoa, and/or parasites. Specific antimicrobial agents may be used to combat specific microbes. Accordingly, a skilled practitioner would know which antimicrobial agent would be relevant or useful depending on the microbe identified, or the symptoms displayed.

In some embodiments, the antimicrobial agent is a protein, a peptide, an antibody, DNA, a carbohydrate, an inorganic molecule, or an organic molecule. In certain embodiments, the antimicrobial agents are antimicrobial small molecules. Typically, antimicrobial small molecules are of relatively low molecular weight, e.g., less than 1,000, or less than 600-700, or between 300-700 molecular weight.

In some embodiments, the antimicrobial agent is an antibacterial agent. In some embodiments, the antibacterial agent treats infections caused by gram positive bacteria. In some embodiments, the antibacterial agent treats infections caused by gram negative bacteria. In some embodiments, the antibacterial agent treats infections caused by mycobacteria. In some embodiments, the antibacterial agent treats infections caused by giardia.

In some embodiments, the antibacterial agent treats infections by inhibiting bacterial protein synthesis. In some embodiments, the antibacterial agent treats infections by disrupting synthesis of bacterial cell wall. In some embodiments, the antibacterial agent treats infections by changing permeability of bacterial cell membranes. In some embodiments, the antibacterial agent treats infections by disrupting DNA replication in bacteria.

In some embodiments, the antibacterial agent is an antibiotic. In some embodiments, the antibiotic is an aminoglycoside. Examples of aminoglycoside antibiotics include and are not limited to amikacin, gentamicin, kanamycin, neomycin, netilmicin, streptomycin, tobramycin, paromycin or the like. In some embodiments, the antibiotic is an ansamycin. Examples of ansamycins include and are not limited to geldanamycin, herbimycin or the like. In some embodiments, the antibiotic is a carbacephem. Examples of carbecephems include and are not limited to loracarbef or the like. In some embodiments, the antibiotic is a carbapenem. Examples of carbapenems include and are not limited to ertapenem, doripenem, imipenem (cilostatin), meropenem or the like. In some embodiments, the antibiotic is a cephalosporin (including, for example, first, second, third, fourth or fifth generation cephalosporins). Examples of cephalosporins include and are not limited to cefaclor, cefamandole, cefotoxin, cefprozil, cefuroxime, cefixime, cefdinir, cefditoren, cefpodoxime, ceftazidime, ceftibuten, ceftizoxime, ceftriaxone, cefepime, ceftobirprole or the like. In some embodiments, the antibiotic is a glycopeptide. Examples of glycopeptides include and are not limited to vancomycin or the like. In some embodiments, the antibiotic is a macrolide antibiotic. Examples of macrolides include and are not limited to azithromycin, clarithromycin, dirithromycin, erythromycin, roxithromycin, troleandomycin, telithromycin, spectinomycin, or the like. In some embodiments, the antibiotic is a monobactam. Examples of monobactams include and are not limited to aztreonam or the like. In some embodiments, the antibiotic is a penicillin. Examples of pencillins include and are not limited to amoxicillin, ampicillin, azociling, carbenicillin, cloxacillin, dicloxacillin, flucloxacillin, mezlocillin, meticillin, nafcillin, oxacillin, peperacillin, ticarcillin or the like. In some embodiments, the antibiotic is a polypeptide. Examples of polypeptide antibiotics include and are not limited to bacitracin, colistin, polymyxin B or the like. In some embodiments, the antibiotic is a quinolone. Examples of quinolones include and are not limited to ciprofloxacin, enoxacin, gatifloxacin, levofloxacin, lomefloxacin, moxifloxacin, nonfloxacin, ofloxacin, trovafloxacin, grepafloxacin, sparfloxacin, AL-15469A, AL-38905 or the like. In some embodiments, the antibiotic is a sulfonamide. Examples of suflonamides include and are not limited to afenide, prontosil, sulfacetamide, sulfamethiazole, sulfanilimide, sulfasalazine, sulfisoxazole, trimethoprim, cotrimoxazole or the like. In some embodiments, the antibiotic is a tetracycline antibiotic. Examples of tetracyclines include and are not limited to demeclocycline, doxycycline, minocycline, oxytetracycline, tetracycline or the like. In some embodiments, the antibiotic is an oxazolidinone antibiotic. Examples of oxazolidinone antibiotics include and are not limited to linezolid or the like. In some embodiments, the antibiotic is arsogebanubem chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin, dalfopristin, rifampicin, thamphenicol, tinidazole or the like.

Antibacterial agents include amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, and combinations thereof.

In some embodiments, an antibiotic compatible with the compositions described herein is a broad spectrum antibiotic. In some embodiments, an antibiotic compatible with the compositions described herein is effective in treating infections that are resistant to other classes of antibiotics. For example, in some instances, vancomycin is effective in treating infections caused by methicillin resistant *Staphylococcus aureus* bacteria. In some embodiments, intratympanic administration of an antibiotic composition described herein reduces the risk of development of antibiotic resistance that is seen with systemic treatments.

In specific embodiments, an antibiotic used in compositions or devices described herein is ciprofloxacin (Cipro). In specific embodiments, an antibiotic used in compositions or devices described herein is gentamicin. In specific embodiments, an antibiotic used in compositions or devices described herein is a penicillin. In specific embodiments, an antibiotic used in compositions or devices described herein is streptomycin.

In some embodiments, an antimicrobial agent is a peptide or a lantibiotic including, by way of example, Maximin H5, Dermcidin, Cecropins, andropin, moricin, ceratotoxin and melittin, Magainin, dermaseptin, bombinin, brevinin-1, esculentins and buforin II, CAP18, LL37, abaecin, apidaecins, prophenin, indolicidin, brevinins, protegrin, tachyplesins, defensins, drosomycin, alamethicin, pexiganan or MSI-78, and other MSI peptides like MSI-843 and MSI-594, polyphemusin, Class I II and III bacterocins like: colicin, pyocin, klebicin, subtilin, epidermin, herbicolacin, brevicin, halocin, agrocin, alveicin, carnocin, curvaticin, divercin, enterocin, enterolysin, erwiniocin, glycinecin, lactococin, lacticin, leucoccin, mesentericin, pediocin, plantaricin, sakacin, sulfolobicin, vibriocin, warnerinand, nisin or the like.

Antiviral agents include acyclovir, famciclovir and valacyclovir. Other antiviral agents include abacavir, aciclovir, adfovir, amantadine, amprenavir, arbidol, atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, imunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

Antifungal agents include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof.

Antiparasitic agents include amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

Antimicrobial agents that are not disclosed herein but which are useful for the amelioration or eradication of otic disorders are expressly included and intended within the scope of the embodiments presented.

Quaternary Ammonium Salt

In some embodiments, the anti-infective agent is a quaternary ammonium salt. In some embodiments, the quaternary ammonium salt comprises C12 or C14 alkyl chain. In some embodiments, the quaternary ammonium salt is not benzalkonium chloride or a polymeric quaternary ammonium salt. In some embodiments, the quaternary ammonium salt is C12-C14-alkyl(ethylbenzyl)dimethylammonium chloride. In some embodiments, the quaternary ammonium salt is C12-alkyl(ethylbenzyl)dimethylammonium chloride. In some embodiments, the quaternary ammonium salt is C14-alkyl(ethylbenzyl)dimethylammonium chloride.

In some aspects, the pharmaceutical composition comprises a quaternary ammonium salt. In some embodiments, the quaternary ammonium salt is a salt of a quaternary ammonium cation. As used herein "quaternary ammonium cations" also known as quats, refer to positively charged polyatomic ions of the structure NR4+, R being an optionally substituted alkyl group or an optionally substituted aryl group. Unlike the ammonium ion (NH4+) and the primary, secondary, or tertiary ammonium cations, the quaternary ammonium cations are permanently charged, independent of the pH of their solution. In some embodiments, the quaternary ammonium salt is not a polymeric quaternary ammonium salt. In some embodiments, the quaternary ammonium salt comprises a C10 or C16 alkyl chain. In some embodiments, the quaternary ammonium salt comprises a C12 or C14 alkyl chain. In some embodiments, the quaternary ammonium salt is not benzalkonium chloride. In some embodiments, the quaternary ammonium salt is C10-C16-alkyl(ethylbenzyl)dimethylammonium chloride. In some embodiments, the quaternary ammonium salt is C12-C14-alkyl(ethylbenzyl)dimethylammonium chloride. In some embodiments, the quaternary ammonium salt is C12-alkyl(ethylbenzyl)dimethylammonium chloride. In some embodiments, the quaternary ammonium salt is substantially pure C12-alkyl(ethylbenzyl)dimethylammonium chloride that is separated from a mixture of C12-C14-alkyl(ethylbenzyl)dimethylammonium chloride. In some embodiments, the quaternary ammonium salt is C12-alkyl(ethylbenzyl)dimethylammonium chloride that is separated from a mixture of C12-C14-alkyl(ethylbenzyl)dimethylammonium chloride and contains less than about 1%, about 2%, about 3%, about 4%, about 5%, about 6%, about 7%, about 8%, about 9%, or about 10% of C14-alkyl(ethylbenzyl)dimethylammonium chloride. In some embodiments, the quaternary ammonium salt, e.g., C12-alkyl(ethylbenzyl)dimethylammonium chloride, does not have any toxicity.

In some embodiments, the C12-C14-alkyl(ethylbenzyl)dimethylammonium chloride is a mixture of C12-alkyl(ethylbenzyl)dimethylammonium chloride and C14-alkyl(ethylbenzyl)dimethylammonium chloride.

In some embodiments, the pharmaceutical composition is essentially free of alkyl(ethylbenzyl)dimethyl ammonium salt having an alkyl of less than 12 carbons or more than 14 carbons.

In some embodiments, the pharmaceutical composition described herein is substantially free of benzalkonium chloride.

In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.5% w/w. In some embodiments, the quaternary ammonium salt, e.g., C12-C14-alkyl(ethylbenzyl)dimethylammonium chloride or C12-alkyl(ethylbenzyl)dimethylammonium chloride is present in the pharmaceutical composition in an amount of about 0.0001%, about 0.0002%, about 0.0003%, about 0.0004%, about 0.0005%, about 0.0006%, about 0.0007%, about 0.0008%, about 0.0009%, about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.01% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.002% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0005% to about 0.002% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0005% to about 0.0012% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount of about 0.001% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount of about 0.0008% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount of about 0.0001%, about 0.0002%, about 0.0003%, about 0.0004%, about 0.0005%, about 0.0006%, about 0.0007%, about 0.0008%, about 0.0009%, about 0.001%, about 0.005%, about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, or about 10% w/w.

In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount between about 10% w/w and about 20% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount between about 10% w/w and about 15% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount between about 15% w/w and about 20% w/w.

In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount of about 10% w/w, about 10.1% w/w, about 10.2% w/w, about 10.3% w/w, about 10.4% w/w, about 10.5% w/w, about 10.6% w/w, about 10.7% w/w, about 10.8% w/w, about 10.9% w/w, about 11% w/w, about 11.10% w/w, about 11.2% w/w, about 11.3% w/w, about 11.4% w/w, about 11.5% w/w, about 11.6% w/w, about 11.7% w/w, about 11.8% w/w, about 11.9% w/w, about 12% w/w, about 12.1% w/w, about 12.2% w/w, about 12.3% w/w, about 12.4% w/w, about 12.5% w/w, about 12.6% w/w, about 12.7% w/w, about 12.8% w/w, about 12.9% w/w, about 13% w/w, about 13.1% w/w, about 13.2% w/w, about 13.3% w/w, about 13.4% w/w, about 13.5% w/w, about 13.6% w/w, about 13.7% w/w, about 13.8% w/w, about 13.9% w/w, about 14% w/w, about 14.1% w/w, about 14.2% w/w, about 14.3% w/w, about 14.4% w/w, about 14.5% w/w, about 14.6% w/w, about 14.7% w/w, about 14.8% w/w, about 14.9% w/w, about 15% w/w, about 15.1% w/w, about 15.2% w/w, about 15.3% w/w, about 15.4% w/w, about 15.5% w/w, about 15.6% w/w, about 15.7% w/w, about 15.8% w/w, about 15.9% w/w, about 16% w/w, about 16.1% w/w, about 16.2% w/w, about 16.3% w/w, about 16.4% w/w, about 16.5% w/w, about 16.6% w/w, about 16.7% w/w, about 16.8% w/w, about 16.9% w/w, about 17% w/w, about 17.1% w/w, about 17.2% w/w, about 17.3% w/w, about 17.4% w/w, about 17.5% w/w, about 17.6% w/w, about 17.7% w/w, about 17.8% w/w, about 17.9% w/w, about 18% w/w, about 18.1% w/w, about 18.2% w/w, about 18.3% w/w, about 18.4% w/w, about 18.5% w/w, about 18.6% w/w, about 18.7% w/w, about 18.8% w/w, about 18.9% w/w, about 19% w/w, about 19.1% w/w, about 19.2% w/w, about 19.3% w/w, about 19.4% w/w, about 19.5% w/w, about 19.6% w/w, about 19.7% w/w, about 19.8% w/w, about 19.9% w/w, or about 20% w/w.

In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.01% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.0001% to about 0.001% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 0.1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 0.01% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 0.1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 1% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 2% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 3% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 4% to about 5% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 1% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 2% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 3% to about 4% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 1% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 2% to about 3% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 1% to about 2% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.001% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.01% to about 1% w/w. In some embodiments, the quaternary ammonium salt, e.g., C12-C14-alkyl(ethylbenzyl)dimethylammonium chloride or C12-alkyl(ethylbenzyl)dimethylammonium chloride, is present in the pharmaceutical composition in an amount ranging from about 0.1% to about 1% w/w.

In some embodiments, the quaternary ammonium salt destroys phospholipids within the microbial cell wall, prompting autolysis and microbial cell entry for an additional antimicrobial agent incorporated in the medical implant composition. In some embodiment, the additional antimicrobial agent is infused or impregnated in the based material through supercritical fluid process disclosed herein, e.g. by combing with the quaternary ammonium salt prior to contact with supercritical fluid or by combining with the supercritical fluid prior to contact with the quaternary ammonium salt. In some embodiment, the additional antimicrobial agent is coated to the medical implant material formed by the process disclosed herein.

Immunosuppressant

In some embodiments, the immunosuppressant agent is a calcineurin inhibitors. In some embodiments, the immunosuppressant agent is selected from the group consisting of cyclosporine, tacrolimus, and pimecrolimus. In some embodiments, the immunosuppressant agent is tacrolimus.

In some embodiments, the immunosuppressant agent is present in the pharmaceutical composition in an amount ranging from about 0.0001% to about 0.5% w/w. In some embodiments, the immunosuppressant agent is present in the pharmaceutical composition in an amount of about 0.0001%, about 0.0002%, about 0.0003%, about 0.0004%, about 0.0005%, about 0.0006%, about 0.0007%, about 0.0008%, about 0.0009%, about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5% w/w. In some embodiments, the immunosuppressant agent is present in the pharmaceutical composition in an amount ranging from about 0.0001% to about 0.1% w/w. In some embodiments, the immunosuppressant agent is present in the pharmaceutical composition in an amount ranging from about 0.0001% to about 0.01% w/w. In some embodiments, the immunosuppressant agent is present in the pharmaceutical composition in an amount ranging from about 0.0001% to about 0.002% w/w. In some embodiments, the immunosuppressant agent is present in the pharmaceutical composition in an amount ranging from about 0.0005% to about 0.002% w/w. In some embodiments, the immunosuppressant agent is present in the pharmaceutical composition in an amount ranging from about 0.0005% to about 0.0012% w/w. In some embodiments, the immunosuppressant agent is present in the pharmaceutical composition in an amount of about 0.001% w/w. In some embodiments, the immunosuppressant agent is present in the pharmaceutical composition in an amount of about 0.0008% w/w. In some embodiments, the immunosuppressant agent is present in the pharmaceutical composition in an amount of about 0.0001%, about 0.0002%, about 0.0003%, about 0.0004%, about 0.0005%, about 0.0006%, about 0.0007%, about 0.0008%, about 0.0009%, about 0.001%, about 0.005%, about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, or about 10% w/w.

In some embodiments, the immunosuppressant agent is present in the pharmaceutical composition in an amount between about 10% w/w and about 20% w/w. In some embodiments, the immunosuppressant agent is present in the pharmaceutical composition in an amount between about 10% w/w and about 15% w/w. In some embodiments, the immunosuppressant agent is present in the pharmaceutical composition in an amount between about 15% w/w and about 20% w/w.

In some embodiments, the immunosuppressant agent is present in the pharmaceutical composition in an amount of about 10% w/w, about 10.1% w/w, about 10.2% w/w, about 10.3% w/w, about 10.4% w/w, about 10.5% w/w, about 10.6% w/w, about 10.7% w/w, about 10.8% w/w, about 10.9% w/w, about 11% w/w, about 11.1% w/w, about 11.2% w/w, about 11.3% w/w, about 11.4% w/w, about 11.5% w/w, about 11.6% w/w, about 11.7% w/w, about 11.8% w/w, about 11.9% w/w, about 12% w/w, about 12.1% w/w, about 12.2% w/w, about 12.3% w/w, about 12.4% w/w, about 12.5% w/w, about 12.6% w/w, about 12.7% w/w, about 12.8% w/w, about 12.9% w/w, about 13% w/w, about 13.1% w/w, about 13.2% w/w, about 13.3% w/w, about 13.4% w/w, about 13.5% w/w, about 13.6% w/w, about 13.7% w/w, about 13.8% w/w, about 13.9% w/w, about 14% w/w, about 14.1% w/w, about 14.2% w/w, about 14.3% w/w, about 14.4% w/w, about 14.5% w/w, about 14.6% w/w, about 14.7% w/w, about 14.8% w/w, about 14.9% w/w, about 15% w/w, about 15.1% w/w, about 15.2% w/w, about 15.3% w/w, about 15.4% w/w, about 15.5% w/w, about 15.6% w/w, about 15.7% w/w, about 15.8% w/w, about 15.9% w/w, about 16% w/w, about 16.1% w/w, about 16.2% w/w, about 16.3% w/w, about 16.4% w/w, about 16.5% w/w, about 16.6% w/w, about 16.7% w/w, about 16.8% w/w, about 16.9% w/w, about 17% w/w, about 17.1% w/w, about 17.2% w/w, about 17.3% w/w, about 17.4% w/w, about 17.5% w/w, about 17.6% w/w, about 17.7% w/w, about 17.8% w/w, about 17.9% w/w, about 18% w/w, about 18.1% w/w, about 18.2% w/w, about 18.3% w/w, about 18.4% w/w, about 18.5% w/w, about 18.6% w/w, about 18.7% w/w, about 18.8% w/w, about 18.9% w/w, about 19% w/w, about 19.1% w/w, about 19.2% w/w, about 19.3% w/w, about 19.4% w/w, about 19.5% w/w, about 19.6% w/w, about 19.7% w/w, about 19.8% w/w, about 19.9% w/w, or about 20% w/w.

In some embodiments, the immunosuppressant agent is present in the pharmaceutical composition in an amount ranging from about 0.0001% to about 5% w/w. In some embodiments, the immunosuppressant agent is present in the pharmaceutical composition in an amount ranging from about 0.0001% to about 4% w/w. In some embodiments, the immunosuppressant agent is present in the pharmaceutical composition in an amount ranging from about 0.0001% to about 3% w/w. In some embodiments, the immunosuppressant agent is present in the pharmaceutical composition in an amount ranging from about 0.0001% to about 2% w/w. In some embodiments, the immunosuppressant agent is present in the pharmaceutical composition in an amount ranging from about 0.0001% to about 1% w/w. In some embodiments, the immunosuppressant agent is present in the pharmaceutical composition in an amount ranging from about 0.0001% to about 0.1% w/w. In some embodiments, the immunosuppressant agent is present in the pharmaceutical composition in an amount ranging from about 0.0001% to about 0.01% w/w. In some embodiments, the immunosuppressant agent is present in the pharmaceutical composition in an amount ranging from about 0.0001% to about 0.001% w/w. In some embodiments, the immunosuppressant agent is present in the pharmaceutical composition in an amount ranging from about 0.001% to about 5% w/w. In some embodiments, the immunosuppressant agent is present in the pharmaceutical composition in an amount ranging from about 0.001% to about 4% w/w. In some embodiments, the immunosuppressant agent is present in the pharmaceutical composition in an amount ranging from about 0.001% to about 3% w/w. In some embodiments, the immunosuppressant agent is present in the pharmaceutical composition in an amount ranging from about 0.001% to about 2% w/w. In some embodiments, the immunosuppressant agent is present in the pharmaceutical composition in an amount ranging from about 0.001% to about 1% w/w. In some embodiments, the immunosuppressant agent is present in the pharmaceutical composition in an amount ranging from about 0.001% to about 0.1% w/w. In some embodiments, the immunosuppressant agent is present in the pharmaceutical composition in an amount ranging from about 0.001% to about 0.01% w/w. In some embodiments, the immunosuppressant agent is present in the pharmaceutical composition in an amount ranging from about 0.01% to about 5% w/w. In some embodiments, the immunosuppressant agent is present in the pharmaceutical composition in an amount ranging from about 0.01% to about 4% w/w. In some embodiments, the immunosuppressant agent is present in the pharmaceutical composition in an amount ranging from about 0.01% to about 3% w/w. In some embodiments, the immunosuppressant agent is present in the pharmaceutical composition in an amount ranging from about 0.01% to about 2% w/w. In some embodiments, the immunosuppressant agent is present in the pharmaceutical composition in an amount ranging from about 0.01% to about 1% w/w. In some embodiments, the immunosuppressant agent is present in the pharmaceutical composition in an amount ranging from about 0.01% to about 0.1% w/w. In some embodiments, the immunosuppressant agent is present in the pharmaceutical composition in an amount ranging from about 0.001% to about 5% w/w. In some embodiments, the immunosuppressant agent is present in the pharmaceutical composition in an amount ranging from about 0.01% to about 5% w/w. In some embodiments, the immunosuppressant agent is present in the pharmaceutical composition in an amount ranging from about 0.1% to about 5% w/w. In some embodiments, the immunosuppressant agent is present in the pharmaceutical composition in an amount ranging from about 1% to about 5% w/w. In some embodiments, the immunosuppressant agent is present in the pharmaceutical composition in an amount ranging from about 2% to about 5% w/w. In some embodiments, the immunosuppressant agent is present in the pharmaceutical composition in an amount ranging from about 3% to about 5% w/w. In some embodiments, the immunosuppressant agent is present in the pharmaceutical composition in an amount ranging from about 4% to about 5% w/w. In some embodiments, the immunosuppressant agent is present in the pharmaceutical composition in an amount ranging from about 0.001% to about 4% w/w. In some embodiments, the immunosuppressant agent is present in the pharmaceutical composition in an amount ranging from about 0.01% to about 4% w/w. In some embodiments, the immunosuppressant agent is present in the pharmaceutical composition in an amount ranging from about 0.1% to about 4% w/w. In some embodiments, the immunosuppressant agent s present in the pharmaceutical composition in an amount ranging from about 1% to about 4% w/w. In some embodiments, the immunosuppressant agent is present in the pharmaceutical composition in an amount ranging from about 2% to about 4% w/w. In some embodiments, the immunosuppressant agent is present in the pharmaceutical composition in an amount ranging from about 3% to about 4% w/w. In some embodiments, the immunosuppressant agent is present in the pharmaceutical composition in an amount ranging from about 0.001% to about 3% w/w. In some embodiments, the immunosuppressant agent is present in the pharmaceutical composition in an amount ranging from about 0.01% to about 3% w/w. In some embodiments, the immunosuppressant agent is present in the pharmaceutical composition in an amount ranging from about 0.1% to about 3% w/w. In some embodiments, the immunosuppressant agent is present in the pharmaceutical composition in an amount ranging from about 1% to about 3% w/w. In some embodiments, the immunosuppressant agent is present in the pharmaceutical composition in an amount ranging from about 2% to about 3% w/w. In some embodiments, the immunosuppressant agent is present in the pharmaceutical composition in an amount ranging from about 0.001% to about 2% w/w. In some embodiments, the immunosuppressant agent is present in the pharmaceutical composition in an amount ranging from about 0.01% to about 2% w/w. In some embodiments, the immunosuppressant agent is present in the pharmaceutical composition in an amount ranging from about 0.1% to about 2% w/w. In some embodiments, the immunosuppressant agent is present in the pharmaceutical composition in an amount ranging from about 1% to about 2% w/w. In some embodiments, the immunosuppressant agent is present in the pharmaceutical composition in an amount ranging from about 0.001% to about 1% w/w. In some embodiments, the immunosuppressant agent is present in the pharmaceutical composition in an amount ranging from about 0.01% to about 1% w/w. In some embodiments, the immunosuppressant agent is present in the pharmaceutical composition in an amount ranging from about 0.1% to about 1% w/w.

Supercritical Fluids and Optional Solvents

Supercritical fluids that may be used to carry out the present invention are, in some embodiments, gases (that is, compounds that are in the form of a gas at atmospheric pressure and 25° C.). Examples of such supercritical fluids include but are not limited to carbon dioxide, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfuoropropane, chloroform, trichloro-fluoromethane, dichloro-difluoromethane, dichloro-tetrafluoroethane) and mixtures thereof. Carbon dioxide is preferred.

The supercritical fluids may be utilized per se or a cosolvent may be included therewith (e.g., in an amount of from 0.01 or 0.1 to 20 or 30 percent by weight or more). Examples of cosolvents include, but are not limited to, water and organic co-solvents. The organic co-solvent may be one compound or a mixture of two or more ingredients. The organic co-solvent may be or comprise an alcohol (including diols, triols, etc.), ether, amine, ketone, carbonate, or alkanes, or hydrocarbon (aliphatic or aromatic) The organic co-solvent may be a mixture of compounds, such as mixtures of alkanes as given above, or mixtures of one or more alkanes in combination with additional compounds such as one or more alcohols as described above. (e.g., from 0 or 0.1 to 5% of a C1 to C15 alcohol (including diols, triols, etc.)). See, e.g., U.S. Pat. No. 6,669,785. The solvent may optionally contain a surfactant, as also described in (for example) U.S. Pat. No. 6,669,785.

The solvent is preferably provided in densified form. This densified form can be a gas at densities greater than 1.1 times the gas density at STP, a liquid (including near-supercritical fluids) or as a densified fluid, these three forms together sometimes being referred to as a "densified" fluid or "densified" gas. See, e.g., U.S. Pat. Nos. 6,860,123; 6,837,611; and 6,755,871.

Utilization of Super Critical Fluid (SCF) methodology to impregnate medical implant materials with antimicrobial and antibiofilm agents, is based upon the novel application of the behavior of supercritical fluids as solvent/antisolvent with co-solvents produced by unique methods to infuse (impregnate) a medical implant material with a desired compound or mixture of compounds, solutions, and materials (infusates, agents, Active Pharmaceutical Ingredient (API) to impart an antimicrobial and antibiofilm property to the material. Impregnation is accomplished using novel equipment and novel methods for utilizing SCF capabilities so as to create a rapid, low cost treatment process which does not markedly increase implant production cost; some examples are, but not limited to: breast augmentation implants with anti-biofilm & anti-infective properties, cannulas and catheters for the urinary tract or circulatory system access with anti-biofilm and antiinfective properties, orthopedic implants including human bone graft donor material with anti-biofilm & anti-infective characteristics, effective strong hernia repair implant meshes with anti-infective properties produced quickly at minimal cost to manufacture.

Anti-Leaching

In some embodiments, the medical implant material disclosed herein retains the bioprotectant impregnated therein for an extended period of time after implantation. In some embodiments, the bioprotectant retained in the medical implant material allows the medical implant material to maintain sufficient mechanical strength and/or structural rigidity over an extended period of time after implantation. Without wishing to be bound by any particular theory, it is contemplated that the bioprotectant impregnated in the medical implant material in some embodiments prevents or reduces microbial attack from the surrounding environment of the medical implant material after implantation. Without wishing to be bound by any particular theory, it is contemplated that the bioprotectant impregnated in the medical implant material in some embodiments prevents or reduces biofilm growth on the medical implant material after implantation.

In some embodiments, the composition retains at least 50% of the bioprotectant 3 days after implantation. In some embodiments, the composition retains at least 60% of the bioprotectant 3 days after implantation. In some embodiments, the composition retains at least 70% of the bioprotectant 3 days after implantation. In some embodiments, the composition retains at least 80% of the bioprotectant 3 days after implantation. In some embodiments, the composition retains at least 90% of the bioprotectant 3 days after implantation. In some embodiments, the composition retains at least 95% of the bioprotectant 3 days after implantation. In some embodiments, the composition retains at least 99% of the bioprotectant 3 days after implantation.

In some embodiments, the composition retains at least 50% of the bioprotectant 5 days after implantation. In some embodiments, the composition retains at least 60% of the bioprotectant 5 days after implantation. In some embodiments, the composition retains at least 70% of the bioprotectant 5 days after implantation. In some embodiments, the composition retains at least 80% of the bioprotectant 5 days after implantation. In some embodiments, the composition retains at least 90% of the bioprotectant 5 days after implantation. In some embodiments, the composition retains at least 95% of the bioprotectant 5 days after implantation. In some embodiments, the composition retains at least 99% of the bioprotectant 5 days after implantation.

In some embodiments, the composition retains at least 50% of the bioprotectant 7 days after implantation. In some embodiments, the composition retains at least 60% of the bioprotectant 7 days after implantation. In some embodiments, the composition retains at least 70% of the bioprotectant 7 days after implantation. In some embodiments, the composition retains at least 80% of the bioprotectant 7 days after implantation. In some embodiments, the composition retains at least 90% of the bioprotectant 7 days after implantation. In some embodiments, the composition retains at least 95% of the bioprotectant 7 days after implantation. In some embodiments, the composition retains at least 99% of the bioprotectant 7 days after implantation.

In some embodiments, the composition retains at least 50% of the bioprotectant 14 days after implantation. In some embodiments, the composition retains at least 60% of the bioprotectant 14 days after implantation. In some embodiments, the composition retains at least 70% of the bioprotectant 14 days after implantation. In some embodiments, the composition retains at least 80% of the bioprotectant 14 days after implantation. In some embodiments, the composition retains at least 90% of the bioprotectant 14 days after implantation. In some embodiments, the composition retains at least 95% of the bioprotectant 14 days after implantation. In some embodiments, the composition retains at least 99% of the bioprotectant 14 days after implantation.

In some embodiments, the composition retains at least 50% of the bioprotectant 4 weeks after implantation. In some embodiments, the composition retains at least 60% of the bioprotectant 4 weeks after implantation. In some embodiments, the composition retains at least 70% of the bioprotectant 4 weeks after implantation. In some embodiments, the composition retains at least 80% of the bioprotectant 4 weeks after implantation. In some embodiments, the composition retains at least 90% of the bioprotectant 4 weeks after implantation. In some embodiments, the composition retains at least 95% of the bioprotectant 4 weeks after implantation. In some embodiments, the composition retains at least 99% of the bioprotectant 4 weeks after implantation.

In some embodiments, the composition retains at least 50% of the bioprotectant 4 weeks after implantation. In some embodiments, the composition retains at least 60% of the bioprotectant 4 weeks after implantation. In some embodiments, the composition retains at least 70% of the bioprotectant 4 weeks after implantation. In some embodiments, the composition retains at least 80% of the bioprotectant 4 weeks after implantation. In some embodiments, the composition retains at least 90% of the bioprotectant 4 weeks after implantation. In some embodiments, the composition retains at least 95% of the bioprotectant 4 weeks after implantation. In some embodiments, the composition retains at least 99% of the bioprotectant 4 weeks after implantation.

In some embodiments, the composition retains at least 50% of the bioprotectant 2 months after implantation. In some embodiments, the composition retains at least 60% of the bioprotectant 2 months after implantation. In some embodiments, the composition retains at least 70% of the bioprotectant 2 months after implantation. In some embodiments, the composition retains at least 80% of the bioprotectant 2 months after implantation. In some embodiments, the composition retains at least 90% of the bioprotectant 2 months after implantation. In some embodiments, the composition retains at least 95% of the bioprotectant 2 months after implantation. In some embodiments, the composition retains at least 99% of the bioprotectant 2 months after implantation.

In some embodiments, the composition retains at least 50% of the bioprotectant 3 months after implantation. In some embodiments, the composition retains at least 60% of the bioprotectant 3 months after implantation. In some embodiments, the composition retains at least 70% of the bioprotectant 3 months after implantation. In some embodiments, the composition retains at least 80% of the bioprotectant 3 months after implantation. In some embodiments, the composition retains at least 90% of the bioprotectant 3 months after implantation. In some embodiments, the composition retains at least 95% of the bioprotectant 3 months after implantation. In some embodiments, the composition retains at least 99% of the bioprotectant 3 months after implantation.

In some embodiments, the composition retains at least 50% of the bioprotectant 6 months after implantation. In some embodiments, the composition retains at least 60% of the bioprotectant 6 months after implantation. In some embodiments, the composition retains at least 70% of the bioprotectant 6 months after implantation. In some embodiments, the composition retains at least 80% of the bioprotectant 6 months after implantation. In some embodiments, the composition retains at least 90% of the bioprotectant 6 months after implantation. In some embodiments, the composition retains at least 95% of the bioprotectant 6 months after implantation. In some embodiments, the composition retains at least 99% of the bioprotectant 6 months after implantation.

In some embodiments, the composition retains at least 50% of the bioprotectant 9 months after implantation. In some embodiments, the composition retains at least 60% of the bioprotectant 9 months after implantation. In some embodiments, the composition retains at least 70% of the bioprotectant 9 months after implantation. In some embodiments, the composition retains at least 80% of the bioprotectant 9 months after implantation. In some embodiments, the composition retains at least 90% of the bioprotectant 9 months after implantation. In some embodiments, the composition retains at least 95% of the bioprotectant 9 months after implantation. In some embodiments, the composition retains at least 99% of the bioprotectant 9 months after implantation.

In some embodiments, the composition retains at least 50% of the bioprotectant 12 months after implantation. In some embodiments, the composition retains at least 60% of the bioprotectant 12 months after implantation. In some embodiments, the composition retains at least 70% of the bioprotectant 12 months after implantation. In some embodiments, the composition retains at least 80% of the bioprotectant 12 months after implantation. In some embodiments, the composition retains at least 90% of the bioprotectant 12 months after implantation. In some embodiments, the composition retains at least 95% of the bioprotectant 12 months after implantation. In some embodiments, the composition retains at least 99% of the bioprotectant 12 months after implantation.

Sustained Release

In some embodiments, the medical implant material disclosed herein releases the bioprotectant impregnated therein to the surrounding environment for an extended period of time after implantation. In some embodiments, the release of the bioprotectant in the medical implant material treats or prevents diseases or conditions associated with implantation, such as immune response, inflammation, etc. In some embodiments, treatment or prevention of the diseases or conditions associated with implantation helps the medical implant material to maintain sufficient mechanical strength and/or structural rigidity over an extended period of time after implantation. Without wishing to be bound by any particular theory, it is contemplated that the bioprotectant released from the medical implant material in some embodiments prevents or reduces immune response against the medical implant material after implantation. Without wishing to be bound by any particular theory, it is contemplated that the bioprotectant released from the medical implant material in some embodiments prevents or reduces inflammation caused or induced by the implantation.

In other or further embodiments, the formulation provides an extended release formulation of at least one antimicrobial agent. In certain embodiments, diffusion of at least one antimicrobial agent from the formulation occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one antimicrobial agent is released from the formulation for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the formulation provides both an immediate release and an extended release formulation of an antimicrobial agent. In yet other embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first antimicrobial agent and an extended release of a second antimicrobial agent or other therapeutic agent. In yet other embodiments, the formulation provides an immediate release and extended release formulation of at least one antimicrobial agent, and at least one therapeutic agent. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first antimicrobial agent and second therapeutic agent, respectively.

In a specific embodiment the formulation provides a therapeutically effective amount of at least one antimicrobial agent at the site of disease with essentially no systemic exposure. In an additional embodiment the formulation provides a therapeutically effective amount of at least one antimicrobial agent at the site of disease with essentially no detectable systemic exposure. In other embodiments, the formulation provides a therapeutically effective amount of at least one antimicrobial agent at the site of disease with little or no detectable systemic exposure.

The combination of immediate release, delayed release and/or extended release antimicrobial agent compositions or formulations may be combined with other pharmaceutical agents, as well as the excipients, diluents, stabilizers, tonicity agents and other components disclosed herein. As such, depending upon the antimicrobial agent used, the thickness or viscosity desired, or the mode of delivery chosen, alternative aspects of the embodiments disclosed herein are combined with the immediate release, delayed release and/or extended release embodiments accordingly.

Medical Implant

In some aspects, a medical device refers to an entity not produced by a body of an individual and performs a function inside or on the surface of the body of the individual. In some embodiments, the medical device is in the body in a temporary basis. In some embodiments, the medical device is an indwelling device. In some embodiments, the medical device is in the body on a permanent basis. In some embodiments, the medical device is an implantable device.

In some embodiments, implantable medical devices include but are not limited to orthopedic implants, joint prostheses, bone fracture fixation devices, cardiac implants, vascular implants, vascular bypass grafts, dental implants, heart valves, heart assist devices, prosthetic implants, ocular implants, stents, surgical staples, biomaterials, bioactive material delivery apparatuses, implantable vascular access ports, vascular conduits, plates, screws, spinal cages, dental fillings, braces, embolic devices, artificial hearts, venous filters, clips, sutures, prosthetic meshes, pacemakers, pacemaker leads, defibrillators, neurostimulators, neurostimulator leads, and implantable or external sensors.

In some embodiments, indwelling medical devices include but are not limited to urinary catheters, vascular catheters, peritoneal catheters, catheters (e.g., central venous catheters and arterial catheters), endotracheal tubes, tracheostomy tube, nasogastric tubes, surgical drain tubes, tubes, central nervous system shunts, guidewires, cannulas, medical ports, intra-aortic balloon pumps, and extra-corporeal devices such as blood oxygenators, blood filters, hemodialysis units, hemoperfusion units and plasmapheresis units. In some embodiments, catheters include but are not limited to intravascular catheters, hemodialysis catheters, urinary catheters, peritoneal dialysis catheters, enteral feeding tubes, gastrostomy tubes, endotracheal tubes, tracheostomy tubes, and umbilical catheters.

In some embodiments, the medical devices are insertable, such as implantable shunts, catheters, or medical ports. In some embodiments, the insertable medical devices are useful in managing movement of fluids, detecting (e.g., assessing, calculating, evaluating, determining, gauging, identifying, measuring, monitoring, quantifying, resolving, or sensing) mechanical, physical, or biochemical information (e.g., the presence of a biomarker, intracranial pressure, blood pressure, a disease state) associated with the individual, draining or collecting body fluids, and/or for administering therapeutics, medications, pharmaceuticals, intravenous fluids, blood products, or delivering parenteral nutrition.

In some embodiments, an orthopedic implant includes implants that span across the skin layers interfacing with an internal tissue, such as a hard tissue like bone, or a soft tissue like muscle or cartilage, or with another implant. In some embodiments, the orthopedic implants include prosthesis parts and accessory components interfacing such prosthesis parts. Generally, the surfaces of the implant are completely or partially implanted into the body of the subject, comprising a metal substrate having one or more surfaces operable to contact a bone tissue or soft tissue when implanted. In some embodiments, the orthopedic implants be permanent tissue replacement devices, permanent stabilization devices, or temporary skeletal stabilization devices.

In some embodiments, the orthopedic implants include joint replacement systems, for hips, knees, elbow, or shoulder joints. In some embodiments, the orthopedic implants include uncemented devices that require tissue ingrowth or ongrowth to stabilize the implant. In some embodiments, the devices do not require biologic fixation, such as fracture stabilization hardware (intramedullary nails, plates, screws), and arthrodesis hardware. In some embodiments, internal and external fixation implants and devices include bone plates, anchors, bone screws, rods, intramedullary nails, arthrodesis nails, pins, wires, spacers, and cages. In some embodiments, the coating be applied to transdermal devices such as external fixation pins used in fracture stabilization or limb lengthening procedures.

Diseases and Conditions Related to Infections from Use of Medical Implants

In some aspects, infections from the use of medical devices pose tremendous problems for patients. In some embodiments, during an infection an infectious agent (e.g., fungi, microorganisms, parasites, pathogens (e.g., viral pathogens, bacterial pathogens), prions, viroids, or viruses)) interferes with the health of an individual. In some embodiments, infections cause chronic wounds, gangrene, loss of an infected tissue, or even death.

Despite sterilization and aseptic procedures, infection remains a major impediment to implantable devices, indwelling devices, and other medical devices. In some embodiments, when the infection does not quickly subside, it is necessary to remove the medical device. Medical device-associated infections result from microorganism adhesion and possibly subsequent biofilm formation proximate an implantation site. In some embodiments, biofilm-forming microorganisms colonize catheter devices at least partially implanted into the individual. In some embodiments, it is difficult to treat and is fatal for the individual if a biofilm-induced infection takes hold.

In some embodiments, microorganisms are present at the site of the medical device use, which include bone or surrounding tissues such as skin, blood, muscle, cartilage, and bone. In some embodiments, microorganisms enter the surgical site and colonize. In some embodiments, microorganisms that colonize the skin at the surgical site enter into the surgical site.

In some aspects, biofilms are involved in a wide variety of medical device-associated infections. In some embodiments, infectious processes in which biofilms have been implicated include common problems such as urinary tract infections, catheter infections, middle-ear infections, formation of dental plaque, gingivitis, coating contact lenses, and infections of permanent indwelling devices such as joint prostheses and heart valves. Bacterial biofilms may impair cutaneous wound healing and reduce topical antibacterial efficiency in healing or treating infected skin wounds. Biofilms in dental plaque may adhere to the teeth and comprise bacteria cells (mainly the Gram positive *Streptococcus mutans* and *Streptococcus sanguinis*) and bacterial extracellular products.

In some embodiments, microorgamisms commonly associated with catheters include without limitation bacteria, *Staphylococcus epidermidis, Staphylococcus aureus, Pseudomonoas aeruginosa, Klebsiella pneumoniae*, Enterobacteriaceae *Enterococcus faecalis*, and fungi, e.g., *Candida albicans* and other *Candida* species. In some embodiments, microorgamisms commonly associated with urinary catheters films include without limitation *S. epidermidis, Enterococcus faecalis, E. coli, Proteus mirabilis, P. aeruginosa, K. pneumoniae*, and other gram-negative organisms.

In some embodiments, the bacteria causing with medical device-associated infection may comprise Enterobacteriales, Bacteriodales, Legionellales, Neisseriales, Pseudomonales, Vibrionales, Pasterrellales, Camylobacterales, *Acinetobacter, Actinobacillus, Bordetella, Brucella, Campylobacter, Cyanobacteria, Enterobacter, Erwinia, Escherichia coli, Franciscella, Helicobacter, Hemophilus, Klebsiella, Legionella, Moraxella, Neisseria, Pasteurella, Proteus, Pseudomonas, Salmonella, Serratia, Shigella, Treponema, Vibrio* and *Yersinia, Klebsiella pneumonia, Acinetobacter baumanii, Pseudomonas aeruginosa, Neisseria gonorrhoeae*, or *Neisseria meningitis, Staphylococcus, Streptococcus, Enterococcus* (including Vancomycin-resistant *Enterococcus faecalis*: VRE), *Bacillus, Listeria, Proteus mirabilis, Staphylococcus saprophyticus, Staphylococcus xylosus, Staphylococcus lugdunensis, Staphylococcus schleiferi, Staphylococcus caprae, Staphylococcus epidermidis, Staphylococcus hominis, Staphylococcus saprophyticus, Staphylococcus wameri, Staphylococcus aureus*, MRSA, *Enterococcus faecalis, Enterococcus faecium, Proprionibacterium acnes, Bacillus cereus, Bacillus subtilis, Listeria monocytogenes, Streptococcus pyogenes, Streptococcus salivarius, Streptococcus mutans* or *Streptococcus pneumoniae*, and *Staphylococcus aureus*, or combinations thereof.

In some embodiments, the microorganism associated with medical device-related infections include without limitation fungi, e.g., *Candida albicans* and other *Candida* species.

Of particular concern are emerging multi-drug resistant gram-negative bacteria for which there are increasingly fewer effective antibiotics. In some embodiments, the Gram negative bacterial infections comrpise Enterobacteriales, Bacteriodales, Legionellales, Neisseriales, Pseudomonales, Vibrionales, Pasterrellales and Camylobacterales. In some embodiments, multidrug resistance of gram-negative bacteria has resistance to at least one extended-spectrum cephalosporin, one aminoglycoside, and ciprofloxacin. In some embodiments, gram-negative bacteria with multidrug resistance comprise *Acinetobacter* spp., *P. aeruginosa, K. pneumoniae*, and *E. cloacae*.

Staphylococcus

Bacteria of the genus *Staphylococcus* are Gram-positive, nonspore forming facultative anaerobes that grow by aerobic respiration or fermentation, with diameters of 0.5-1.5 μm. They are characterized by individual cocci, which divide in more than one plane to form grape-like clusters.

*Staphylococcus* comprises up to two-thirds of all pathogens in orthopedic implant infections and they are the principal causative agents of two major types of infection affecting bone-septic arthritis and osteomyelitis, which involve the inflammatory destruction of joint and bone; these infections are difficult to treat because of the ability of the organisms to form small colonies and to grow into biofilms. Many *Staphylococcus* strains, particularly *S. epidermidis* and some *S. aureus* strains, produce biofilm.

Staphylococcus aureus

*Staphylococcus aureus* is an important nosocomial pathogen, able to cause a variety of human disease conditions. It can often be found as a commensal and a transient or persistent part of the resident flora of the skin and anterior nares in a large proportion (20-50%) of the human population. However, when cutaneous/mucous barriers are breached, severe and at times life threatening infections can develop. Nosocomial infections by *S. aureus* are particularly frequent in immuno-compromised and severely debilitated patients, and prevail in the presence of indwelling medical devices.

Treatment of *S. aureus* infections is often complex, namely due to the emergence of methicillin-resistant *S. aureus* (MRSA) strains and resistance to other classes of antibiotics. Because of its pathogenic potential and complexity of its treatment, MRSA has received more attention than its methicillin-sensitive counterpart (MSSA). MRSAs are resistant to β-lactam antibiotics (oxacillin, penicillin and amoxicillin), including third generation cephalosporins, streptomycin, tetracycline and sulfonamides; and upon exposure to vancomycin and other glycopeptide antibiotics, certain MRSA strains become less susceptible to these antibiotics.

*S. aureus* possesses several cell-surface adhesion molecules that facilitate its binding to bone matrix. Binding involves a family of adhesins that interact with extracellular matrix (ECM) components and these adhesins have been termed microbial surface components recognizing adhesive matrix molecules (MSCRAMMs). Specific MSCRAMMs are needed for the colonization of specific tissues and for the adhesion to biomaterials and to the ECM proteins deposited on the biomaterial surface. Particular MSCRAMMs include fibronectin-binding proteins, fibrinogen-binding proteins, elastin-binding adhesin and collagen-binding adhesin. A number of these adhesins have already been thoroughly investigated and identified as critical virulence factors implicated in various phases of infection, including early colonization, invasion, tissue localization and cell internalization.

In recent years, the polysaccharide intercellular adhesin (PIA) has been found in many *S. aureus* strains, and is required for biofilm formation and bacterium-bacterium adhesion. This adhesin is responsible for the production of the extracellular polysaccharide matrix that makes up the biofilm. It is known that once a biofilm has formed, the bacteria within the biofilm are protected from phagocytosis and antibiotics.

*S. aureus* produces virulence factors to facilitate disease causation, and rapidly develops antimicrobial resistance. The cell-surface virulence factors include the microbial surface components recognizing adhesive matrix molecules (MSCRAMMs) as receptors in the human host, other surface proteins, polysaccharide intercellular adhesin and capsular polysaccharides. The cell-surface MSCRAMMs typically are produced during exponential growth phase. The role of these various virulence factors is to provide nutrients required for survival in the host, and microbial cell protection from the host immune system during lesion formation. The secreted virulence factors, typically produced during the post-exponential and stationary phases, include a large group of exoenzymes, such as proteases, glycerol ester hydrolase (lipase) and nucleases that make nutrients available to the microorganism.

Staphylococcus epidermidis

*Staphylococcus epidermidis* is the most frequently isolated member of the group of coagulase-negative staphylococci (CoNS) from implant-associated infections and they are associated with nosocomial or hospital-acquired infections, and have been found to be more antibiotic resistant than *S. aureus*. This group is diagnostically distinguished from *S. aureus* by its inability to produce coagulase.

*S. epidermidis* very often becomes the major infective agent in compromised patients, such as drug abusers and immuno-compromised patients (patients under immunosuppressive therapy, AIDS patients and premature newborns). The entry door into the human body in all of these infections is usually an intravascular catheter. The pathogenesis of implant-associated *S. epidermidis* infections is characterized by its ability to colonize a surface and form a thick, multilayered biofilm, often referred to as slime. This biofilm is composed of an extracellular polysaccharide known as polysaccharide intercellular adhesin (PIA), which is essential for *S. epidermidis* biofilm formation. PIA production is also known to protect *S. epidermidis* from phagocytosis and other major components of the host defense system. Generally, the success of *S. epidermidis* as a pathogen has to be attributed to its ability to adhere to surfaces and to remain there, under the cover of a protecting extracellular material, in relative silence.

*S. epidermidis* does not produce many toxins and tissue damaging exoenzymes, as does *S. aureus*. To date, few ECM recognizing adhesins have been identified for *S. epidermidis*; however, adhesins to fibronectin, fibrinogen, vitronectin and collagen have been identified.

Bone Tissue Infections

Bone tissue infections, namely osteomyelitis, septic arthritis and prosthetic joint infections (PJI), still represent the worst complications of orthopedic surgery and traumatology. The main pathways of infection for osteomyelitis, septic arthritis and PJI are either hematogenous, resulting from bacteremia; contiguous, when the infection is transmitted from local tissue; or direct, resulting from infiltration of bone, often following injury, surgery or implantation of a foreign body, such as joint replacement.

Osteomyelitis

Osteomyelitis describes a range of infections in which bone is colonized with microorganisms, with associated inflammation and bone destruction. The occurrence, type, severity, and clinical prognosis of osteomyelitis depend on the interplay of a triad of factors, including the characteristics and virulence of the infecting pathogen, the properties of the host, and the source of infection.

The most common etiologic agents causing osteomyelitis are *Staphylococcus aureus, Pseudomonas aeruginosa, Staphylococcus epidermidis* and *Escherichia coli*. Historically, *S. aureus* has been the dominant pathogen for all classes of osteomyelitis, accounting for 45 percent of infections; however, the appearance of the microorganism dropped to 27 percent by 1988.

The establishment of osteomyelitis begins with the infiltration of microorganisms into the body. Early infections are usually related to trauma or contamination during surgery; however, a number of improvements in surgical procedures have been responsible for reducing the infection rate. Late infections, which may not occur until after a number of months postoperatively, can also result from bacterial contamination during trauma, surgery or via remote infections. In many of these cases, bacteria introduced during trauma or surgery became dormant for an extended period of time.

Haematogenous osteomyelitis most frequently affects children and the elderly. In children, the incidence is typically between 1 in 5,000 and 1 in 10,000. It has been argued that the incidence of hematogenous osteomyelitis is decreasing with an annual fall in childhood cases of 0.185 per 100,000 people recorded in Glasgow, Scotland between 1970 and 1997. Conversely, osteomyelitis resulting from direct infection is reported as being increased. This is probably due to motor-vehicle accidents and the increasing use of orthopedic fixation devices and total joint implants.

Implanted biomaterials can act as an avenue for both bacterial contamination and colonization toward the development of osteomyelitis. The mechanisms of infection are quite complex and vary with the species of bacteria. If the conditions are favorable, bacteria create an initial attachment to the surface. A permanent attachment develops as protein adhesin-receptor form along with a polysaccharide film after the distance between the cell and the surface is sufficiently reduced. Because biomaterials do not elicit an antiphagocytic reaction toward bacteria after adhesion, these are able to multiply and colonize freely on implant surfaces.

Septic Arthritis

Septic arthritis is a joint disease typified by bacterial colonization and rapid joint destruction and it manifests as a serious infection characterized by pain, fever, swelling and even loss of function in one or more affected joints. The most commonly involved joints are the knees and hips.

In all age and risk groups, the most frequent causative organisms identified are *Staphylococcus aureus* followed by other gram-positive bacteria, including streptococci.

Numerous different factors have been identified for developing of septic arthritis. These factors include rheumatoid arthritis or osteoarthritis, joint prosthesis, low socioeconomic status, intravenous drug abuse, alcoholism, diabetes, previous intra-joint corticosteroid injection and cutaneous ulcers.

The yearly incidence of septic arthritis is between 2 and 10 in 100,000 in the general population but it may be as high as 30-70 per 100,000 in rheumatoid arthritis patients or recipients of prosthetic joints 42-44 and is more common in children than in adults, and in males rather than in females. The incidence of septic arthritis seems to be rising, and this increase is linked to augmented orthopedic-related infection 46 and an aging population, more invasive procedures being undertaken and enhanced use of immunosuppressive treatment.

Mortality for septic arthritis varies in different studies, but seems to be around 11% for monoarticular sepsis. In view of the 11% mortality rate for septic arthritis, patients should be admitted to hospital for prompt assessment, supportive care and intravenous antibiotic treatment, along with measures to aspirate pus from the joint.

Prosthetic Joint Infections

The implantation of prosthetic joints along with the use of other implantable orthopedic devices (e.g., pins, screws, plates and external fixators) has improved the quality of life greatly and restored function to patients suffering from debilitating bone and joint disease or injury. Based on conservative estimates, millions of people worldwide have some form of prosthetic joint or other implantable orthopedic device. Among the possible complications associated with implantation, infection is the most serious and occurs in 1 to 13 percent of the cases; the resulting consequences include postoperative prosthesis failure, chronic pain and immobility.

Prosthetic joint infections (PJIs) occur less frequently than aseptic failures but represent the most devastating complication. These infections are a major threat, as therapy is difficult, resulting in a significant increase in hospitalization-related morbidity and mortality.

The most common agents are *Staphylococcus aureus* and *Staphylococcus epidermidis*, which account for close to 65% of PJIs. They are the most commonly reported microorganisms both in early and late infections and in total knee and hip arthroplasty.

Non-Limiting Embodiments

1. A medical implant composition, comprising:
   a base material having a surface portion and an interior portion; and
   an bioprotectant incorporated throughout the base material, wherein at least a part of the interior portion of the base material is impregnated with the bioprotectant.
2. The composition of Embodiment 1-2, wherein the base material is a surgical mesh material.
3. The composition of Embodiment 1-3, wherein the base material is a plastic, a polypropylene, polyester, polytetrafluoroethylene (PTFE), decellularized tissue, bone, tooth, a biosynthetic polymer, or any combination thereof.
4. The composition of Embodiment 1-4, wherein the bioprotectant is an immunosuppressant agent or an anti-infective agent.
5. The composition of Embodiment 4, wherein the anti-infective agent is an anti-microbial agent, an anti-biofilm agent, or a combination thereof.
6. The composition of Embodiment 4, wherein the anti-infective agent is a quaternary ammonium salt.
7. The composition of Embodiment 6, wherein the quaternary ammonium salt comprises C12 or C14 alkyl chain.
8. The composition of Embodiment 6, wherein the quaternary ammonium salt is not benzalkonium chloride or a polymeric quaternary ammonium salt.
9. The composition of Embodiment 6, wherein the quaternary ammonium salt is C12-C14-alkyl(ethylbenzyl)dimethylammonium chloride.
10. The composition of Embodiment 6, wherein the quaternary ammonium salt is C12-alkyl(ethylbenzyl)dimethylammonium chloride.
11. The composition of Embodiment 6, wherein the quaternary ammonium salt is C14-alkyl(ethylbenzyl)dimethylammonium chloride.
12. The composition of Embodiment 4, wherein the immunosuppressant agent is a calcineurin inhibitors.
13. The composition of Embodiment 4, wherein the immunosuppressant agent is selected from the group consisting of cyclosporine, tacrolimus, and pimecrolimus.
14. The composition of Embodiment 4, wherein the immunosuppressant agent is tacrolimus.
15. The composition of Embodiment 1-14, wherein the bioprotectant is heterogeneously impregnated throughout the medical implant material.
16. The composition of Embodiment 1-14, wherein the bioprotectant is homogeneously impregnated throughout the medical implant material.
17. The composition of Embodiment 1-15, wherein the at least 30% of the interior portion of the base material is impregnated with the bioprotectant.
18. The composition of Embodiment 1-15, wherein the at least 50% of the interior portion of the base material is impregnated with the bioprotectant.
19. The composition of Embodiment 1-15, wherein the at least 60% of the interior portion of the base material is impregnated with the bioprotectant.

20. The composition of Embodiment 1-15, wherein the at least 70% of the interior portion of the base material is impregnated with the bioprotectant.
21. The composition of Embodiment 1-20, wherein the composition provides sustained release of the bioprotectant from the composition for at least 7 days upon implantation.
22. The composition of Embodiment 1-20, wherein the composition provides sustained release of the bioprotectant from the composition for at least 14 days upon implantation.
23. The composition of Embodiment 1-20, wherein the composition provides sustained release of the bioprotectant from the composition for at least 4 weeks upon implantation.
24. The composition of Embodiment 1-20, wherein the composition provides sustained release of the bioprotectant from the composition for at least 12 weeks upon implantation.
25. The composition of Embodiment 1-24, wherein the composition retains at least 50% of the bioprotectant 3 days after implantation.
26. The composition of Embodiment 1-24, wherein the composition retains at least 70% of the bioprotectant 3 days after implantation.
27. The composition of Embodiment 1-24, wherein the composition retains at least 90% of the bioprotectant 3 days after implantation.
28. The composition of Embodiment 1-24, wherein the composition retains at least 90% of the bioprotectant 7 days after implantation.
29. The composition of Embodiment 1-24, wherein the composition retains at least 90% of the bioprotectant 14 days after implantation.
30. The composition of Embodiment 1-24, wherein the composition retains at least 90% of the bioprotectant 28 days after implantation.
31. The composition of Embodiment 1-30, wherein the composition is present in, and provides structural strength to, a medical implant.
32. The composition of Embodiment 31, wherein the medical implant is selected from the group consisting of a surgical mesh, a breast augmentation implant, a cannula, a catheter, an orthopedic implant, or a hernia repair implant.
33. The composition of Embodiment 31, wherein medical implant is a surgical mesh.
34. The composition of Embodiment 33, wherein the surgical mesh is a synthetic mesh, an acellular mesh, or a hybrid mesh comprising an acellular mesh and a synthetic mesh.
35. The composition of Embodiment 31 wherein medical implant is a breast augmentation implant.
36. The composition of Embodiment 1-35, wherein the composition is prepared by a process comprising: contacting the based material and the bioprotectant with supercritical fluid carbon dioxide (SCF—$CO_2$) in an enclosure under an elevated pressure to allow the bioprotectant to impregnate at least a part of the interior portion of the base material.
37. The composition of Embodiment 36, wherein the process further comprises reducing the pressure within the enclosure after at least a part of the interior portion of the base material is impregnated with the bioprotectant.
38. The composition of Embodiment 36-37, wherein the base material and bioprotectant are placed in the enclosure before SCF—$CO_2$ enters the enclosure.
39. The composition of Embodiment 36-37, wherein the bioprotectant is combined with SCF—$CO_2$ to form a mixture before the mixture contacts the base material in the enclosure.
40. The composition of Embodiment 36-39, wherein the elevated pressure is from about 500 psi to about 6000 psi.
41. The composition of Embodiment 36-40, wherein the elevated pressure is from about 500 psi to about 2500 psi.
42. The composition of Embodiment 36-40, wherein the elevated pressure is from about 1000 psi to about 2500 psi.
43. The composition of Embodiment 36-40, wherein the elevated pressure is from about 1000 psi to about 2000 psi.
44. The composition of Embodiment 36-40, wherein the elevated pressure is from about 1500 psi to about 2000 psi.
45. The composition of Embodiment 41, wherein temperature in the enclosure is from about 15° C. to about 60° C.
46. The composition of Embodiment 41, wherein temperature in the enclosure is from about 30° C. to about 55° C.
47. The composition of Embodiment 41, wherein temperature in the enclosure is from about 40° C. to about 50° C.
48. The composition of Embodiment 41, wherein base material comprises decellularized tissue.
49. The composition of Embodiment 36-40, wherein the elevated pressure is from about 2500 psi to about 6000 psi.
50. The composition of Embodiment 36-40, wherein the elevated pressure is from about 3000 psi to about 6000 psi.
51. The composition of Embodiment 36-40, wherein the elevated pressure is from about 3000 psi to about 5000 psi.
52. The composition of Embodiment 36-40, wherein the elevated pressure is from about 4000 psi to about 5000 psi.
53. The composition of Embodiment 49, wherein temperature in the enclosure is from about 60° C. to about 160° C.
54. The composition of Embodiment 49, wherein temperature in the enclosure is from about 80° C. to about 150° C.
55. The composition of Embodiment 49, wherein temperature in the enclosure is from about 110° C. to about 130° C.
56. The composition of Embodiment 49, wherein base material comprises polypropylene.
57. The composition of Embodiment 36-56, wherein the contact of the base material and the bioprotectant with SCF—$CO_2$ occurs for a period of from about 1 minute to about 24 hours.
58. The composition of Embodiment 36-56, wherein the contact of the base material and the bioprotectant with SCF—$CO_2$ occurs for a period of from about 5 minutes to about 10 hours.
59. The composition of Embodiment 36-56, wherein the contact of the base material and the bioprotectant with SCF—$CO_2$ occurs for a period of from about 5 minutes to about 8 hours.
60. A method of preparing a medical implant composition, comprising:
 (i) placing the base material in an enclosure, wherein the base material comprises a surface portion and an interior portion;

(ii) allowing supercritical fluid carbon dioxide (SCF—$CO_2$) to flow into the enclosure and contact the base material in the presence of a bioprotectant at an elevated pressure;

(iii) reducing pressure in the enclosure after at least a part of the interior portion of the base material is impregnated with the bioprotectant.

61. The method of Embodiment 60, wherein the base material and bioprotectant are placed in the enclosure before SCF—$CO_2$ enters the enclosure.
62. The method of Embodiment 60, wherein the bioprotectant is combined with SCF—$CO_2$ to form a mixture before the mixture contacts the base material in the enclosure.
63. The method of Embodiment 60-62, wherein the elevated pressure is from about 500 psi to about 6000 psi.
64. The composition of Embodiment 63, wherein the elevated pressure is from about 500 psi to about 2500 psi.
65. The method of Embodiment 63, wherein the elevated pressure is from about 1000 psi to about 2500 psi.
66. The method of Embodiment 63, wherein the elevated pressure is from about 1000 psi to about 2000 psi.
67. The method of Embodiment 63, wherein the elevated pressure is from about 1500 psi to about 2000 psi.
68. The method of Embodiment 63-67, wherein temperature in the enclosure is from about 15° C. to about 60° C. during the contact.
69. The method of Embodiment 63-67, wherein temperature in the enclosure is from about 30° C. to about 55° C. during the contact.
70. The method of Embodiment 63-67, wherein temperature in the enclosure is from about 40° C. to about 50° C. during the contact.
71. The method of Embodiment 64-70, wherein base material comprises decellularized tissue.
72. The method of Embodiment 63, wherein the elevated pressure is from about 2500 psi to about 6000 psi.
73. The method position of Embodiment 63, wherein the elevated pressure is from about 3000 psi to about 6000 psi.
74. The method of Embodiment 63 wherein the elevated pressure is from about 3000 psi to about 5000 psi.
75. The method of Embodiment 63, wherein the elevated pressure is from about 4000 psi to about 5000 psi.
76. The method of Embodiment 72-75, wherein temperature in the enclosure is from about 60° C. to about 160° C. during the contact.
77. The method of Embodiment 72-75, wherein temperature in the enclosure is from about 80° C. to about 150° C. during the contact.
78. The method of Embodiment 72-75, wherein temperature in the enclosure is from about 110° C. to about 130° C. during the contact.
79. The method of Embodiment 72-77, wherein base material comprises polypropylene.
80. The method of Embodiment 60-79, wherein the contact of the base material and the bioprotectant with SCF—$CO_2$ occurs for a period of from about 1 minute to about 24 hours.
81. The method of Embodiment 60-79, wherein the contact of the base material and the bioprotectant with SCF—$CO_2$ occurs for a period of from about 5 minutes to about 10 hours.
82. The method of Embodiment 60-79, wherein the contact of the base material and the bioprotectant with SCF—$CO_2$ occurs for a period of from about 5 minutes to about 8 hours.
83. The method of Embodiment 60-82, wherein the contact of SCF—$CO_2$ with the base material occurs in the presence of the bioprotectant and a solvent.
84. The method of Embodiment 83, wherein the solvent is combined with bioprotectant prior to the contact of SCF—$CO_2$ with the base material.
85. The method of Embodiment 83, wherein the solvent is combined with SCF—$CO_2$ prior to the contact of SCF—$CO_2$ with the base material in the presence of the bioprotectant.
86. The method of Embodiment 60-85, wherein the base material is a surgical mesh material.
87. The method of Embodiment 60-85, wherein the base material is a plastic, a polypropylene, polyester, polytetrafluoroethylene (PTFE), decellularized tissue, bone, tooth, a biosynthetic polymer, or any combination thereof.
88. The method of Embodiment 60-87, wherein the bioprotectant is an immunosuppressant agent or an anti-infective microbial agent.
89. The method of Embodiment 88, wherein the anti-infective agent is an anti-microbial agent, an anti-biofilm agent, or a combination thereof.
90. The method of Embodiment 88, wherein the anti-infective agent is a quaternary ammonium salt.
91. The method of Embodiment 90, wherein the quaternary ammonium salt comprises C12 or C14 alkyl chain.
92. The method of Embodiment 90, wherein the quaternary ammonium salt is not benzalkonium chloride or a polymeric quaternary ammonium salt.
93. The method of Embodiment 90, wherein the quaternary ammonium salt is C12-C14-alkyl(ethylbenzyl)dimethyl-ammonium chloride.
94. The method of Embodiment 90, wherein the quaternary ammonium salt is C12-alkyl(ethylbenzyl)dimethylammonium chloride.
95. The method of Embodiment 90, wherein the quaternary ammonium salt is C14-alkyl(ethylbenzyl)dimethylammonium chloride.
96. The method of Embodiment 88, wherein the immunosuppressant agent is a calcineurin inhibitors.
97. The method of Embodiment 88, wherein the immunosuppressant agent is selected from the group consisting of cyclosporine, tacrolimus, and pimecrolimus.
98. The method of Embodiment 88, wherein the immunosuppressant agent is tacrolimus.
99. The method of Embodiment 60-98, wherein the bioprotectant is heterogeneously impregnated throughout the medical implant material.
100. The method of Embodiment 60-98, wherein the bioprotectant is homogeneously impregnated throughout the medical implant material.
101. The method of Embodiment 60-100, wherein the at least 30% of the interior portion of the base material is impregnated with the bioprotectant.
102. The method of Embodiment 60-100, wherein the at least 50% of the interior portion of the base material is impregnated with the bioprotectant.
103. The method of Embodiment 60-100, wherein the at least 60% of the interior portion of the base material is impregnated with the bioprotectant.
104. The method of Embodiment 60-100, wherein the at least 70% of the interior portion of the base material is impregnated with the bioprotectant.
105. The method of Embodiment 60-104, further comprising forming a medical implant with the medical implant composition, wherein the composition is present in, and provides structural strength to, the medical implant.

106. The method of Embodiment 105, wherein the medical implant is selected from the group consisting of a surgical mesh, a breast augmentation implant, a cannula, a catheter, an orthopedic implant, or a hernia repair implant.
107. The method of Embodiment 105, wherein medical implant is a surgical mesh.
108. The method of Embodiment 107, wherein the surgical mesh is a synthetic mesh, an acellular mesh, or a hybrid mesh comprising an acellular mesh and a synthetic mesh.
109. The method of Embodiment 105, wherein medical implant is a breast augmentation implant.

The present invention is further explained in greater detail in the following non-limiting Examples.

Example 1—Method of Incorporating Bioprotectant into Medical Implant

Supercritical Fluid Carbon Dioxide (SCF—$CO_2$) in used in this invention applied by novel technology, other gases that exhibit super critical behavior can be substituted as desired. The properties of various gases to behave as liquids at certain (critical) conditions of temperature and pressure has long been characterized. SCF can be used to extract numerous components from materials, including organic matter (such as caffeine from coffee beans). The ability of SCF—$CO_2$ to remove cellular material from tissue has been demonstrated by various methods other than this invention. This method produces an acellular, sterile implant material in a single step on any tissue used as starting substrate. Subsequent agent impregnation is similar with both biologic or synthetic target materials, conditions and parameters are matched in specific.

Supercritical Fluid Carbon Dioxide (SCF—$CO_2$) is used as an Anti-Solvent (SAS) in mass transfer action to impregnate a bioprotectant (e.g. antimicrobial agents, anti-biofilm agents, immunosuppressants) of interest into to a target substrate (medical implant biologic or synthetic). Various forms of Super Critical Conditions (SCC) are created by proprietary methods including pre-pressure density enhancement of chosen SCF compound by "density packing" and subsequent pressurization to desired SCF conditions by thermal manipulation in a sealed chamber which contains the sample containment platform cage whereby the target substrate (implant material) is exposed to SCF—$CO_2$. In some embodiments, ethanol can be combined with SCF—$CO_2$ before introduction into the reaction enclosure/chamber/vessel. In some embodiments, a controlled reaction including with immersion in desired infusate may be conducted at specific temperature, pressure, and time for required target substrate implant material (mesh) impregnation and reaction. Other sequences of extraction, dissolution, and impregnation may be conducted to meet requirements of target materials and selected infusates.

When the infusing/impregnation process is completed, SCF release is carefully controlled to achieve desired results, either by passive expansion or pump assisted flow. Modifying agent co-solvents (ethanol, etc.) may be employed in the SAS process and variations include the modified methods of RESS (rapid expansion of supercritical solutions) and RESOLV (rapid expansion of supercritical solutions into a liquid solvent) to encompass the many varieties of target compounds of interest in relation to a wide variety of target substrates materials. Although SCF—$CO_2$ is the principle agent of use, other acceptable SCF behavior compounds may be employed solely or as co-solvents as required to achieve useful goals.

In some embodiments, the SCF process disclosed herein impregnate the entire structure of an implant, polymer or biologic scaffold graft with the bioprotectant. In some embodiments, the SCF process disclosed herein also provides the additional benefit of decellularization of a tissue. In addition, the ability to provide Drug Delivery (controlled release or sustained release of the bioprotectant) to the local area is beneficial. By specific methods of controlled Super Critical State Fluid enhanced Mass Transfer, in one configuration of the invention, a condition of supersaturation can be achieved such that an API will be delivered by diffusion and mobilization chemical mechanisms such that a large amount of API is delivered locally over a short period and residual compound elutes over months. Other approaches can be formed by addition of additives such as—cyclodextrins which can act to encage hydrophobic compounds and sequester them away from aqueous phase environments, likewise 2-aminoimidazole derivatives, brominated furanones, benzimidazoles, and several other agents such as peptides that inhibit biofilm formation may be employed in this process.

The method of the invention may be carried out by first, combining the drug with the polymer and optionally an excipient(s) to form a mixture. This mixing step may be carried out by any suitable technique or in any suitable apparatus, such as an enclosure. Next, the mixture is contacted under pressure with a densified gas solvent as described above to form the composite material. The step of combining the mixture with the solvent can be carried out by any suitable technique or in any suitable apparatus.

Step 1 Sample is loaded into the enclosure that enables supercritcal fluids to flow into and out of the enclosure with cellular material. Optionally, solid $CO_2$ is also loaded into the enclosure.

Step 2 Supercritical $CO_2$ is pumped/pressurized into enclosure cools down and pressure in vessel decreases then Supercritical $CO_2$, this is repeated three times.

Step 3 The solid $CO_2$ previously loaded in vessel sublimes further increasing vessel pressure up to 1,500 psig.

Step 4 Vessel is heated up to 40° C. to 200° C. depending upon material of interest to be treated.

Step 5 Pressure increases to 2,000 psig thru 5,000 psig as heat is added.

Step 6 The sample is allowed to sit in batch mode or can be in steady-state mode where $CO_2$, ethanol and additive (antibiotic, etc.) is injected.

Step 7 After 5 minutes up to 8 hours the vessel is then depressurized.

Step 8 The enclosure is opened and decellularized sample (for biological use case) removed.

Step 9 The cellular material removed is either at bottom of vessel for removal or has been flowed out of the vessel in steady-state mode.

Optional Secondary coatings. Drug/polymer composites prepared as described above may optionally be coated (e.g., by spraying, dipping, or any suitable technique) with a second material. In some embodiments, the second material comprises an additional bioprotectant, such as an antimicrobial agent or an anti-biofilm agent. In some embodiments, the second material comprises one or more excipients to aid in the subsequent binding, forming, dispersion, structure or drug-elution profile of the drug/polymer composite. This second material can be any of several different chemical functionalities and several different functions in the resulting drug/polymer composite material. For example, the second material can be a pharmaceutical excipient, providing a means to alter the pharmacological effect of the drug or providing a means to alter the release profile of the drug-delivery. In some embodiments the second material can be a $CO_2$-philic material. In this case an additional process step can be utilized where after compressive forming of the part, a second condition of densified fluid can be used to remove the $CO_2$-philic material, thereby forming pores in and rendering porosity to the formed part.

Example 2—Abdominal Ventral Hernia Mesh

There are over 350,000 ventral hernia repairs (VHR) performed annually in the U.S. at a total cost exceeding $3.2 billion. It is estimated that 30% or more of these patients will experience a recurrence of their hernia and associated co-morbidities within five years of their initial surgery. Currently, nearly all of all ventral hernias are repaired by reinforcing the wound site with an implanted mesh due to studies which reveal a 50% reduction in hernia recurrence if a supportive implant mesh is used vs suture repair. A very large percentage of ventral abdominal hernias are contaminated due to the high incidence of stomas, fistulas, concurrent GI surgery, or other scenarios. The 5 year recurrence rate of ventral hernia can be up to 30%. One of the major factors in hernia recurrence is surgical site infection (SSI) which may lead to breakdown of repair and extrusion of mesh implant; SSI occurs in up to 18% of cases. Novel approaches to ameliorate SSI and mesh loss are direly needed. There are numerous materials utilized in mesh construction both synthetic and biologic, polypropylene plastic being the most common material. Mesh materials provide strength to support the hernia repair but may exhibit incomplete healing and provide a nexus for infection. The application of antimicrobial agents to mesh structures has been employed with some success and trials of coating of antimicrobial agents to mesh materials have shown promise. However, a superior solution of coating mesh materials to provide antimicrobial activity and improve hernia repair survival has yet to be accomplished. Use of novel application technology to impregnate mesh materials may provide a homogeneous matrix that possesses the characteristics which are a deterrent to infection while retaining the necessary support strength for long term hernia repair. This invention proposes to address this need by use of the superior capabilities of supercritical fluid solvent/anti-solvent mass transfer action to modify medical implant materials for improved outcomes.

In this experiment, 25 mm squares of Bard mesh implant material (synthetic plastic with biologic coating) were used for study. Using SuperCritical Fluid Carbon Dioxide (SCF—$CO_2$) with ethanol solvent, a concentration 100 ug/ml of Tacrolimus (FK-506) was included in an infusion solution of ethanol solvent and distilled, deionized water of 50 ml volume—the solution also included 4 mg/ml of tetracycline to observe chemical behavior of the antibiotic. The SCF process continued for 4 hours before pressure was released to obtain the drug-impregnated mesh material (Composition A). As a control experiment, 25 mm squares of Bard mesh implant material (synthetic plastic with biologic coating) was solution-coated with the same Tacrolimus solution of equal time exposure at room temperature and pressure (Composition B).

Figure 11:
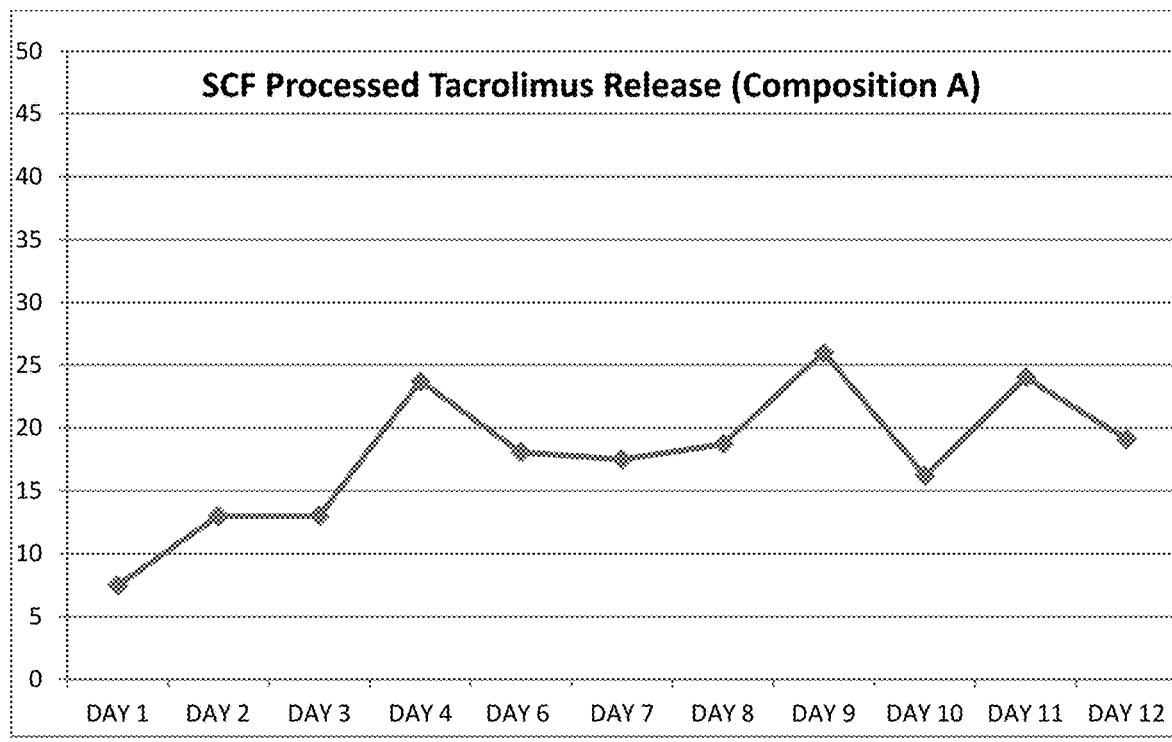
FIG. 11 shows drug elusion profile of Composition A according to Example 2 (Week 1and Week 2)
Figure 12:
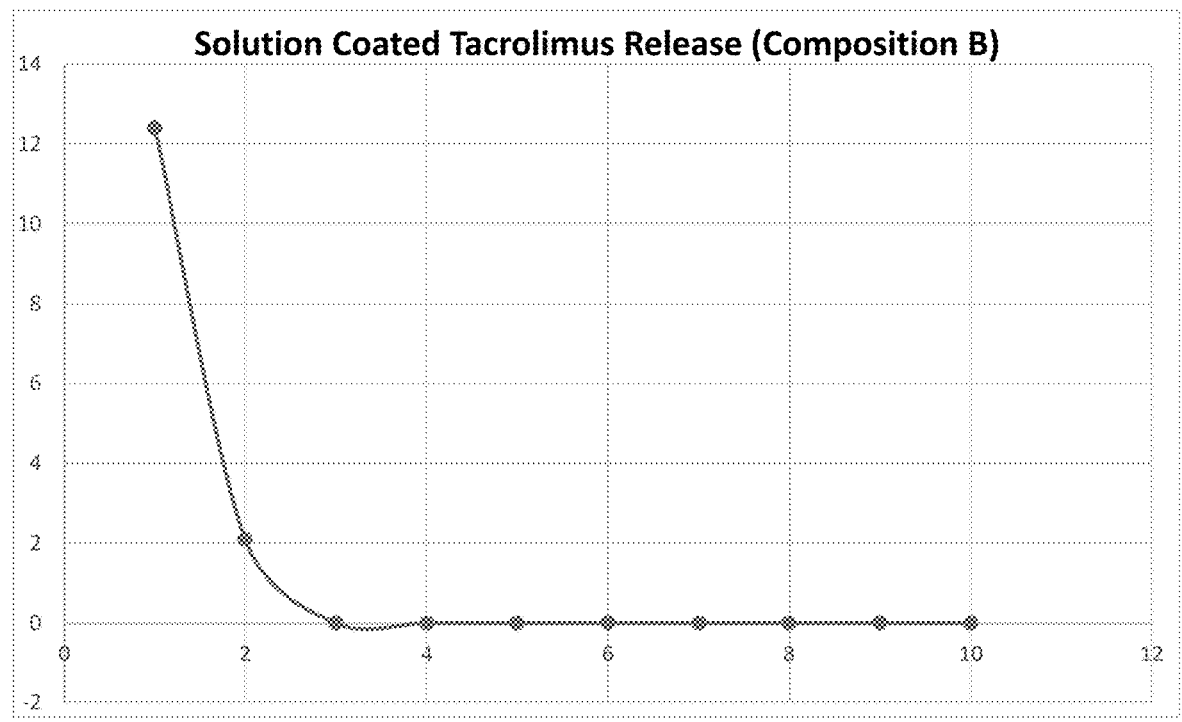
FIG. 12 shows drug elusion profile of Composition B according to Example 2 (Week 1and Week 2)

The release of the tacrolimus from Composition A and Composition B is monitored over two weeks. As shown in FIG. 11, the SCF-processed mesh implant material provides sustained release of the bioprotectant (e.g. tacrolimus) over the two-week period. In contrast, the solution coated mesh implant material released almost all tacrolimus during the first two days, as shown in FIG. 12.

Figure 13:
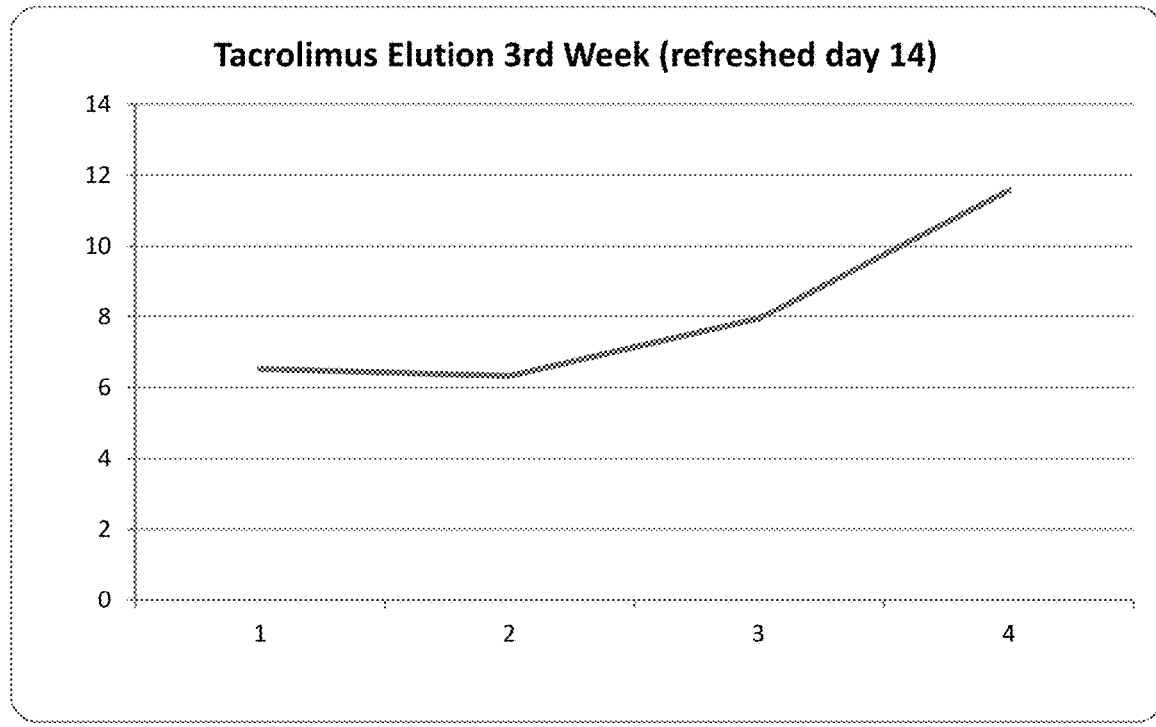
FIG. 13 shows drug elusion profile of Composition A according to Example 2 (Week 1and Week 2)
Figure 14:
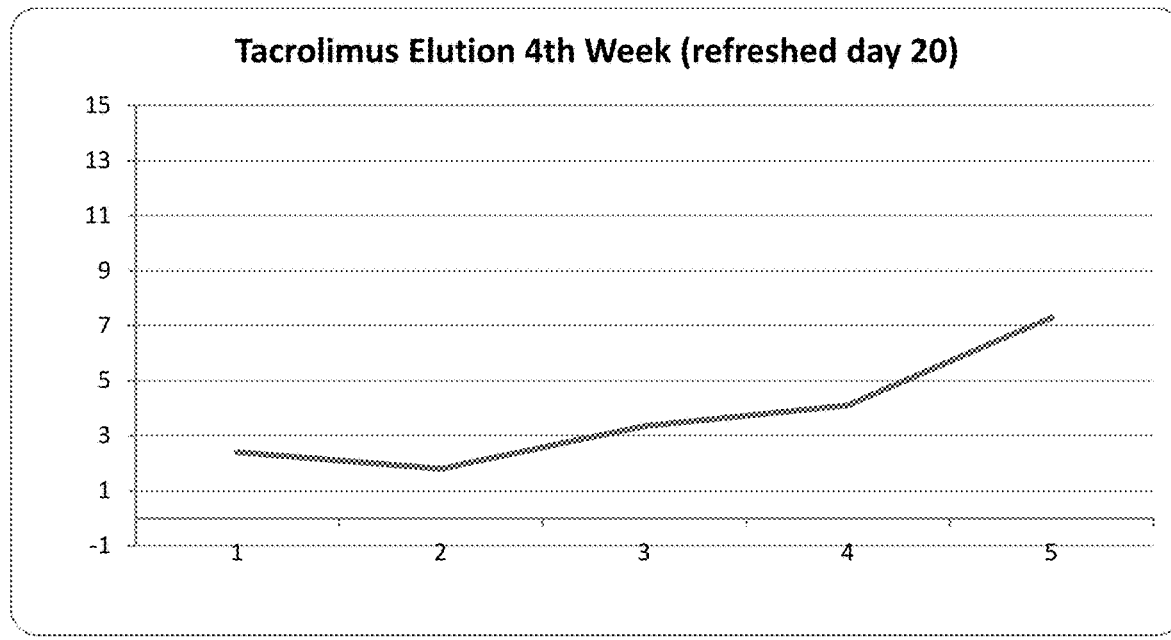
FIG. 14 shows drug elusion profile of Composition A according to Example 2 (Week 1and Week 2)

To further investigate the sustained release, the 50 mL PBS solution is refreshed at the beginning of third week while the daily aliquot analysis continues. As shown in FIG. 13, the SCF-processed mesh implant material provides sustained release of the bioprotectant (e.g. tacrolimus) during the third weeks. At the beginning of week 4, the 50 mL PBS solution is refreshed again and the daily aliquot analysis continues. As shown in FIG. 14, the SCF-processed mesh implant material continues to provide sustained release of the bioprotectant (e.g. tacrolimus) during the fourth weeks as well.

Figure 15:
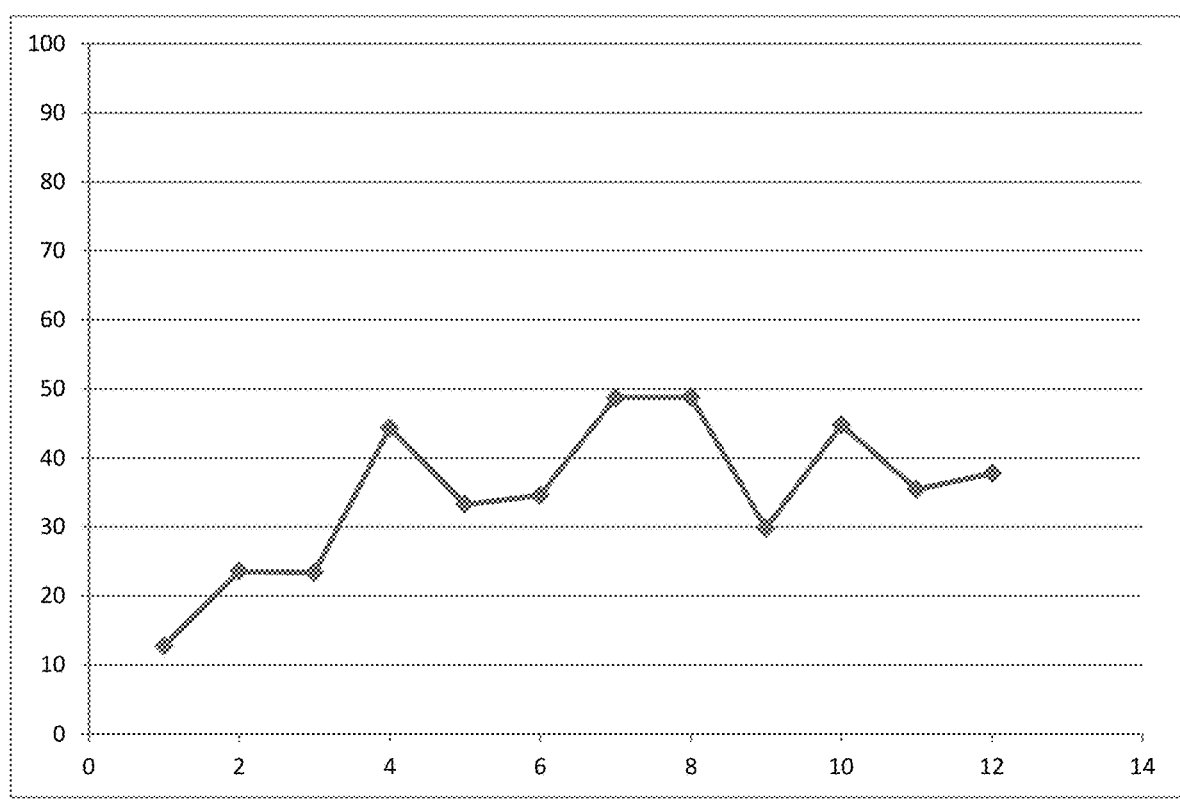
FIG. 15 shows drug elusion profile of Composition C according to Example 3 (Week 1and Week 2).

In addition to the mesh implant material, similar sustained release experiments were performed on breast implant material infused or impregnated with tacrolimus according to the SCF process disclosed herein. As shown in FIG. 15, the SCF-processed breast implant material provides sustained release of the bioprotectant (e.g. tacrolimus) for at least a week and beyond.

Example 3—Characterization of SCF-Processed Implant Material

1. Cellular tissue and matrix were processed in supercritical fluid vessel, the decellularized mass weighed less than the non-decellularized mass and there was residual cellular material outside of the enclosure that held the original sample of material to be decellularized.

2. Graft material (e.g. surgical graft) was processed in the supercritical fluid vessel within an enclosure chamber with an antibiotic and a dye. In parallel the surgical graft reference was soaked in antibiotic and dye outside of the supercritical fluid vessel within an enclosure chamber (sample holder within vessel). The processed supercritical fluid graft and the reference case graft were then soaked in varying % of ethanol and % of water solution to allow the antibiotic and dye to leach out; then observed under microscope as well as mass spectrometry. Based upon microscope and mass spectrometry the supercritical fluid processed graft material was embedded (internally and externally) with antibiotic and dye. Therefore, its antibiotic and dye properties persisted past the leaching test and therefore experiment successful in providing enhanced antibiotic/microbial impregnation of graft and polymer material.

3. Bone material (human bone) was processed in the supercritical fluid vessel within an enclosure chamber with an antibiotic and a dye. in parallel the bone reference was soaked in antibiotic and dye outside of the supercritical fluid vessel within an enclosure chamber (sample holder within vessel). The processed supercritical fluid bone and the reference case bone were then soaked in varying % of ethanol and % of water solution to allow the antibiotic and dye to leach out; then observed under microscope as well as mass spectrometry. Based upon microscope and mass spectrometry the supercritical fluid processed bone material was embedded (internally and externally) with antibiotic and dye. Therefore, its antibiotic and dye properties persisted past the leaching test and therefore experiment successful in providing enhanced antibiotic/microbial impregnation of the bone material 4. The same bone supercritical test would be applicable for teeth as well to better decontaminate and impregnate teeth with decell, sterilize and antimicrobial or other additive (pigment, etc.) within dental industry.

5. Sustained release assay conducted by daily aliquot analysis by LC-MS of the 50 ml PBS holding solution (phosphate buffered saline) in closed top centrifuge tubes (Falcon type), refreshed daily until end of study.

The foregoing is illustrative of the present invention, and is not to be construed as limiting thereof. The invention is defined by the following claims, with equivalents of the claims to be included therein.

What is claimed is:

1. A method of preparing a medical implant composition, comprising:
   (i) placing the base material in an enclosure, wherein the base material comprises a surface portion and an interior portion;
   (ii) allowing supercritical fluid carbon dioxide ($SCF-CO_2$) to flow into the enclosure and contact the base material in the presence of a bioprotectant at an elevated pressure; and
   (iii) reducing pressure in the enclosure after at least 30% of the interior portion of the base material is impregnated with the bioprotectant,
   wherein the base material is polypropylene or decellularized tissue.

2. The method of claim 1, wherein the base material and bioprotectant are placed in the enclosure before $SCF-CO_2$ enters the enclosure.

3. The method of claim 1, wherein the bioprotectant is combined with $SCF-CO_2$ to form a mixture before the mixture contacts the base material in the enclosure.

4. The method of claim 1 wherein the elevated pressure is from about 500 psi to about 6000 psi.

5. The composition of claim 4, wherein the elevated pressure is from about 500 psi to about 2500 psi.

6. The method of claim 5, wherein temperature in the enclosure is from about 15° C. to about 60° C. during the contact.

7. The method of claim 6, wherein base material comprises decellularized tissue.

8. The method of claim 4, wherein the elevated pressure is from about 2500 psi to about 6000 psi.

9. The method of claim 8, wherein temperature in the enclosure is from about 60° C. to about 160° C.

10. The method of claim 9, wherein base material comprises polypropylene.

11. The method of claim 1, wherein the contact of the base material and the bioprotectant with $SCF-CO_2$ occurs for a period of from about 1 minute to about 24 hours.

12. The method of claim 1, wherein the contact of the base material and the bioprotectant with $SCF-CO_2$ occurs for a period of from about 5 minutes to about 8 hours.

13. The method of claim 1, wherein the contact of $SCF-CO_2$ with the base material occurs in the presence of the bioprotectant and a solvent.

14. The method of claim 13, wherein the solvent is combined with bioprotectant prior to the contact of $SCF-CO_2$ with the base material.

15. The method of claim 13, wherein the solvent is combined with $SCF-CO_2$ prior to the contact of $SCF-CO_2$ with the base material in the presence of the bioprotectant.

16. The method of claim 1, wherein the base material is a surgical mesh material.

17. The method of claim 1, wherein the base material is decellularized bone tissue.

18. The method of claim 1, wherein the bioprotectant is an immunosuppressant agent or an anti-infective agent.

19. The method of claim 18, wherein the anti-infective agent is an anti-microbial agent, an anti-biofilm agent, or a combination thereof.

20. The method of claim 18, wherein the anti-infective agent is a quaternary ammonium salt.

21. The method of claim 20, wherein the quaternary ammonium salt comprises C12 or C14 alkyl chain.

22. The method of claim 20, wherein the quaternary ammonium salt is C12-C14-alkyl(ethylbenzyl)dimethylammonium chloride.

23. The method of claim 18, wherein the immunosuppressant agent is a calcineurin inhibitors.

24. The method of claim 18, wherein the immunosuppressant agent is selected from the group consisting of cyclosporine, tacrolimus, and pimecrolimus.

25. The method of claim 18, wherein the immunosuppressant agent is tacrolimus.

26. The method of claim 1, wherein the bioprotectant is impregnated throughout the medical implant material.

27. The method of claim 1, wherein at least 50% of the interior portion of the base material is impregnated with the bioprotectant.

28. The method of claim 1, wherein at least 60% of the interior portion of the base material is impregnated with the bioprotectant.

29. The method of claim 1, wherein at least 70% of the interior portion of the base material is impregnated with the bioprotectant.

* * * * *